United States Patent
Genberg et al.

(10) Patent No.: US 12,070,467 B2
(45) Date of Patent: Aug. 27, 2024

(54) METHOD OF TREATING CILIATED TISSUE USING CSA MICELLES

(71) Applicants: Carl Genberg, Las Vegas, NV (US); Paul B. Savage, Mapleton, UT (US)

(72) Inventors: Carl Genberg, Las Vegas, NV (US); Paul B. Savage, Mapleton, UT (US)

(73) Assignee: Brigham Young University, Provo, UT (US)

( * ) Notice: Subject to any disclaimer, the term of this patent is extended or adjusted under 35 U.S.C. 154(b) by 486 days.

(21) Appl. No.: 16/979,487

(22) PCT Filed: Mar. 7, 2019

(86) PCT No.: PCT/US2019/021232
§ 371 (c)(1),
(2) Date: Sep. 9, 2020

(87) PCT Pub. No.: WO2019/173642
PCT Pub. Date: Sep. 12, 2019

(65) Prior Publication Data
US 2021/0361672 A1    Nov. 25, 2021

Related U.S. Application Data

(60) Provisional application No. 62/640,010, filed on Mar. 7, 2018.

(51) Int. Cl.
*A61K 31/56*    (2006.01)
*A61K 47/10*    (2017.01)

(52) U.S. Cl.
CPC .............. *A61K 31/56* (2013.01); *A61K 47/10* (2013.01)

(58) Field of Classification Search
CPC ...... A61K 31/56; A61K 47/10; A61K 9/0073; A61K 9/08; A61K 31/575; A61P 31/10; A61P 31/04
See application file for complete search history.

(56) References Cited

U.S. PATENT DOCUMENTS

| | | | |
|---|---|---|---|
| 2013/0022651 A1* | 1/2013 | Savage | A61L 31/145 514/182 |
| 2013/0236619 A1 | 9/2013 | Savage | |
| 2014/0271761 A1 | 9/2014 | Savage et al. | |
| 2015/0110767 A1* | 4/2015 | Savage | A61K 38/14 514/182 |
| 2015/0258121 A1 | 9/2015 | Darien et al. | |
| 2016/0022702 A1 | 1/2016 | Savage et al. | |
| 2017/0258963 A1 | 9/2017 | Savage et al. | |
| 2018/0272034 A1 | 9/2018 | Savage et al. | |

OTHER PUBLICATIONS

Farres et al., "CSA-131, a ceragenin active against colistin-resistant Acinetobacter baumannii and Pseudomonas aeruginosa clinical isolates", International Journal of Antimicrobial Agents, vol. 46, No. 5, Sep. 7, 2015, pp. 568-571.
Hashemi et al., "Antibacterial and Antifungal Activities of Poloxamer Micelles Containing Ceragenin CSA-131 on Ciliated Tissues", Molecules, vol. 23, Mar. 7, 2018.
K. Leszczynska et al., "Potential of ceragenin CSA-13 and its mixture with pluronic F-127 as treatment of topical bacterial infections", Journal of Applied Microbiology, vol. 110, No. 1, Oct. 21, 2010, pp. 229-238.
Nagant et al., "Effect of pluronic acid F-127 on the toxicity towards eukaryotic cells of CSA-13, a cationic steroid analogue of antimicrobial peptides", Journal of Applied Microbiology, vol. 112, No. 6, Apr. 20, 2012, pp. 1173-1183.

* cited by examiner

*Primary Examiner* — David Browe
(74) *Attorney, Agent, or Firm* — Workman Nydegger

(57) ABSTRACT

The present disclosure describes treatment compositions and methods for preventing and/or treating microbial infections of ciliated tissues, such as tissues of the trachea, lungs, and sinuses. The method utilizes a treatment composition that includes a cationic steroidal antimicrobial (CSA) compound, a poloxamer, and a carrier, which is administered to ciliated tissue, such as lung tissue, in order to prevent or treat a microbial infection by killing microbes associated with the ciliated tissue. The poloxamer forms micelles that encapsulate the CSA compound, the poloxamer being included in the treatment composition in an amount, by weight, that is about 100 to 1000 times the amount of the CSA compound.

20 Claims, 19 Drawing Sheets

CSA-1

CSA-2

CSA-3

CSA-4

CSA-5

CSA-6

CSA-7

CSA-8

CSA-10

CSA-11

CSA-90

CSA-91

CSA-92

CSA-92 FL

CSA-93

CSA-94

CSA-95

CSA-96

CSA-105

CSA-106

CSA-107

CSA-109

CSA-110

CSA-112

CSA-113

CSA-118

CSA-119

CSA-120

CSA-121

CSA-121a

CSA-122

CSA-123

CSA-124

CSA-130

CSA-131

CSA-132

Harvested trachea

Sectioned into 2 x 1 cm explants

Transferred to 24 well plate and treated with CSA-131 w/o PF-127 for 1 h

Transferred to 6-well plate with arrangement shown

Measurement of bead clearance over time

METHOD OF TREATING CILIATED TISSUE USING CSA MICELLES

BACKGROUND

The present invention relates to methods of treating ciliated tissues using micelles containing cationic steroidal antimicrobial (CSA) compounds.

CSA compounds (also known as ceragenin compounds) have been shown to be effective in treating diseases and infections in mammals caused by microbes. The effectiveness of CSA compounds in treating diseases and infections caused by microbes can be dependent on the concentration of the CSA compound(s) within a CSA-containing composition and/or the amount of CSA-containing composition administered.

While lower concentrations of antimicrobial CSA compounds are effective in killing planktonic microbes, such as bacteria and fungi, higher concentrations may be needed to fully eradicate biofilm forms of pathogens. In biofilm form, microorganisms enter a sessile state where some cells remain viable even after most other cells have been eradicated by applied antimicrobials.

Epithelial cells appear to tolerate CSA compounds well. However, epithelial cells in the trachea and in other places in the body include cilia. The cilia are fragile and can easily be damaged by antimicrobials and mechanical stresses. At relatively high concentrations, CSA-containing compositions have been found to be cytotoxic to ciliated cells, and therefore harmful to the mammal being treated. In the context of treating such ciliated tissues, it is often difficult to strike the correct balance between effectiveness in killing microbes, on the one hand, and safety to the mammal being treated, on the other. This challenge is aggravated in the case of a biofilm infection, where higher concentrations of antimicrobial agent are required for effective treatment but such higher concentrations may kill, deactivate and/or cause detachment of cilia.

Accordingly, there is a need for improved methods of treating ciliated tissues using CSA-containing compositions that increase or maintain their efficacy in killing microbes, while, at the same time, reducing or minimizing damage to the ciliated cells being treated.

SUMMARY

Disclosed herein are methods of treating ciliated tissues using CSA-containing compositions that maintain or increase efficacy in killing microbes while reducing or minimizing cytotoxicity to mammalian cells.

CSA compounds, which are generally believed to be soluble in various solvents, such as water, saline solution, or ethanol, can undesirably form agglomerates rather than remaining as a highly dispersed solute or colloidal dispersion. In some cases, CSA agglomerates form rapidly. In other cases, CSA compounds can form agglomerates over time after being initially dissolved or dispersed in a solvent or carrier liquid (e.g., after days, weeks, or months). Formation of CSA agglomerates can reduce efficacy because only CSA molecules on the agglomerate surfaces are generally available to interact with and kill microbes, which can essentially remove or sequester a substantial portion of otherwise active CSA molecules from the composition. In addition, CSA compounds and agglomerates can sometimes be cytotoxic by collecting on tissue and forming localized areas of high CSA concentration rather than remaining highly dispersed throughout the CSA-containing composition.

It has now been found that negative effects caused by the previously unknown problem of CSA toxicity and instability can be offset by forming micelles within the solvent or carrier liquid using a suitable amphiphilic compound or composition that is able to encapsulate the CSA molecules and reduce or prevent agglomeration within the composition. Examples of suitable micelle-forming amphiphilic compounds or compositions include one or more surfactants having separate hydrophobic and hydrophilic regions, including poloxamers, such as the poloxamer sold under the trade name PLURONIC F127. Because CSA molecules are themselves amphiphilic and often behave as surfactants, the realization that utilizing a different amphiphilic compound or surfactant within the solvent or carrier liquid to form micelles that can encapsulate the CSA molecules and reduce or prevent agglomeration within the composition was not previously recognized nor readily apparent.

Further, it has now been found that combinations of a poloxamer surfactant and CSA compounds decreases cytotoxicity to ciliated cells without substantially impairing antibacterial and antifungal activity. Without being bound to a particular theory, it is believed that the mechanism of decreased toxicity to ciliated cells is due to transient encapsulation of CSAs in micelles formed by the poloxamer. While ensconced in micelles, CSAs are less prone to associate with host membranes, yet retain high affinity to microbial membranes. In this manner, the micelles act to amplify the membrane selectivity of the CSA compounds in favor of interaction with microbial cell membranes. Such selectivity is particularly beneficial in the case of ciliated tissue, which are highly sensitive to CSAs. For example, where a patient's lungs are infected with a pathogenic biofilm, it may be difficult if not impossible to complete eradicate the infectious biofilm without also destroying lung cilia, which can be more acutely fatal to the patient than the infection.

In some embodiments, a treatment composition used to treat ciliated tissue includes (1) a carrier; (2) CSA compound; and (3) a poloxamer. The CSA compound is preferably included at a concentration of at least about 5 µg/ml. Particularly effective results have been shown when treating ciliated lung and trachea epithelial tissue using a concentration of about 50 µg/ml to about 100 µg/ml. Such concentrations were able to provide effective antimicrobial activity against bacterial and fungal biofilms without significantly disrupting ciliary function. In other implementations, higher or lower CSA concentrations may be suitable. For example, in some circumstances the CSA composition may be included at a concentration of up to about 150 µg/ml or even 200 µg/ml without significantly disrupting the ciliary function of treated tissue. In other implementations, a CSA concentration as low as 10 µg/ml, 20 µg/ml, 30 µg/ml, or 40 µg/ml may be sufficient to treat a particular infection.

The carrier may be water, saline solution, a buffer, other pharmaceutically acceptable carriers, or combinations thereof. Particularly preferred carriers include compositions known in the art which are suitable for administration via inhalation and/or suitable for use in conjunction with a nebulizer.

The poloxamer may be included at a concentration of about 0.5% to about 20%, or about 0.75% to about 15%, or about 1% to about 10% by weight of the treatment composition. At high CSA concentrations of 100 µg/ml, a treatment composition with a poloxamer concentration of 5% was shown to be no different than the control in its effects on ciliary activity. Treatment compositions with lower poloxamer concentrations also exhibited significant reductions in ciliary disruption relative to a treatment composition omitting poloxamer. Nonetheless, such compositions still possessed similar antimicrobial activity as CSA compositions without micelles. By comparison, CSA compositions with high concentrations of CSA without micelles, or at insufficiently low poloxamer concentration, were found to be highly toxic to cilia without significant increase in antimicrobial activity. The ability of CSA compositions with micelles to effectively kill microbes, including biofilms, at high concentrations while being non-toxic to cilia, is surprising and unexpected.

The concentration of poloxamer utilized may be determined according to protective effects desired or required in the treatment composition based on the concentration of CSA compound included, with higher concentrations of CSA corresponding to higher concentrations of poloxamer. The poloxamer may be included in an amount proportional to the amount of CSA compound. For example, the poloxamer may be included in an amount, by weight, that is about 100 to 1000 times, or about 250 to 750 times, or about 500 the amount of CSA compound, by weight. Treatment compositions that include the poloxamer and the CSA compound in these proportioned ratios can effectively balance the need to kill infecting microbes without significantly harming ciliary function. In a preferred embodiment, the poloxamer is the poloxamer sold under the trade name PLURONIC F-127, though other poloxamers may additionally or alternatively be used according to particular application needs.

Beneficially, the treatment of ciliated tissues using CSAs encapsulated in poloxamer micelles allows use of higher concentrations of CSA compound without negatively impacting cilia function. This is particularly beneficial for treating biofilms, as it allows use of CSA concentrations that are high enough to effectively kill the biofilm microbes without causing damage to the cilia that would otherwise occur if the CSA compounds were not provided in combination with a poloxamer.

The CSA micelle treatment compositions described herein may be utilized to treat ciliated tissue. In one embodiment, a method of treating ciliated tissue comprises: (1) providing a treatment composition as described herein having a CSA compound, a poloxamer, and a carrier; (2) administering the treatment composition to ciliated tissue of a subject in need thereof; and (3) the treatment composition killing microbes associated with the ciliated tissue without significantly disrupting ciliary function. In the case of lung infections, the CSA micelle compositions can be administered via inhalation. In other embodiments, CSA compositions can be administered by other routes, such as direct application, irrigation, lavage, injection, infusion, and the like.

Additional features and advantages will be set forth in part in the description that follows, and in part will be obvious from the description, or may be learned by practice of the embodiments disclosed herein. The objects and advantages of the embodiments disclosed herein will be realized and attained by means of the elements and combinations particularly pointed out in the appended claims. It is to be understood that both the foregoing brief summary and the following detailed description are exemplary and explanatory only and are not restrictive of the embodiments disclosed herein or as claimed.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings, in which.

DETAILED DESCRIPTION

I. Introduction

Figure 1A:
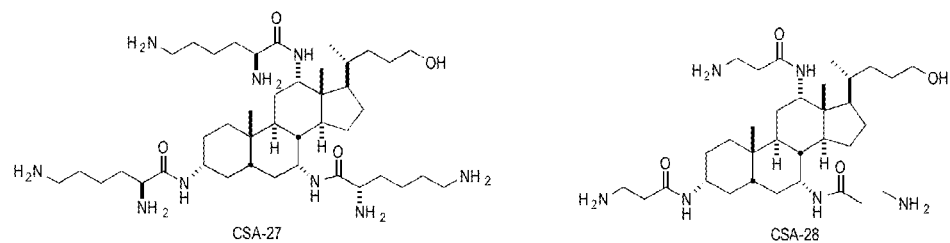
FIG. 1A illustrates exemplary hydrolysable cationic steroidal anti-microbial ("CSA") compounds.
Figure 1A:
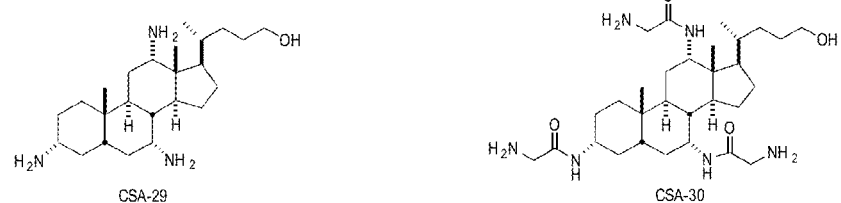
Figure 1A:
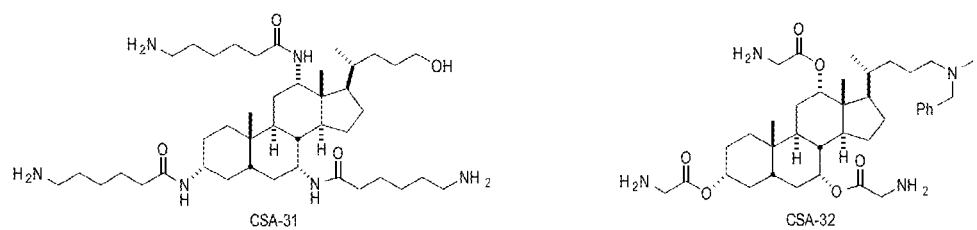
Figure 1A:
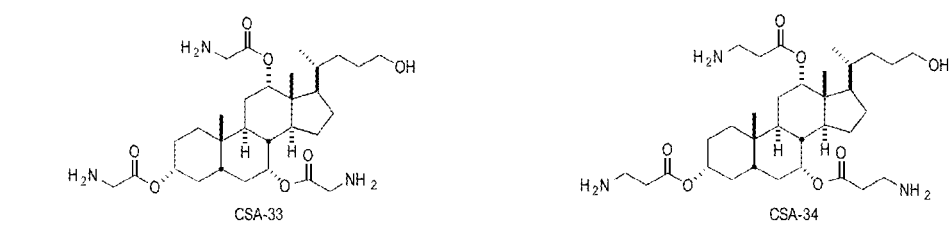
Figure 1A:
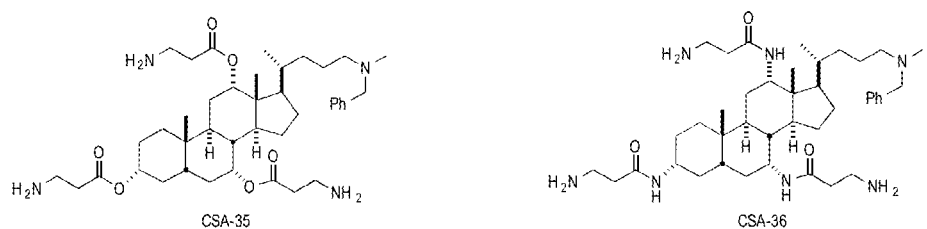
Figure 1A:
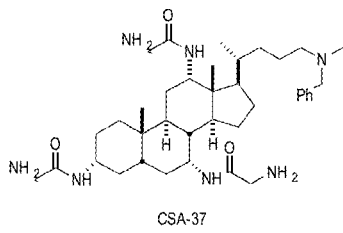
Figure 1A:
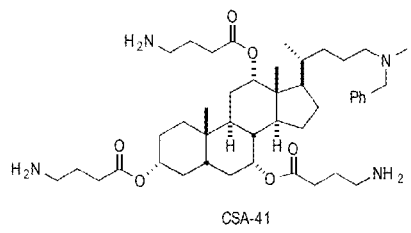
Figure 1A:
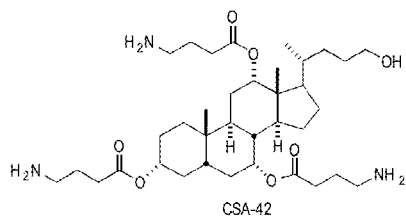
Figure 1A:
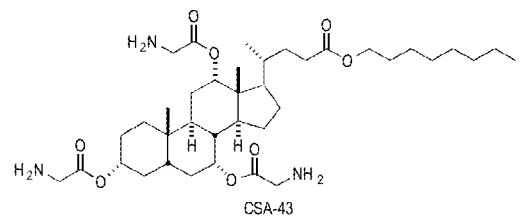
Figure 1A:
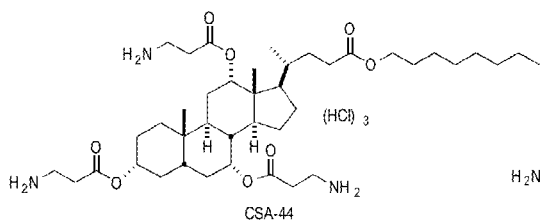
Figure 1A:
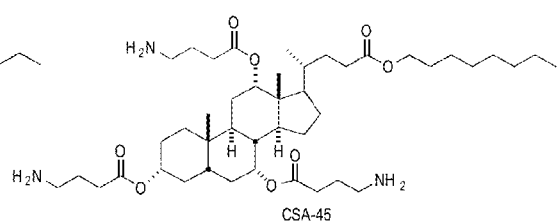
Figure 1A:
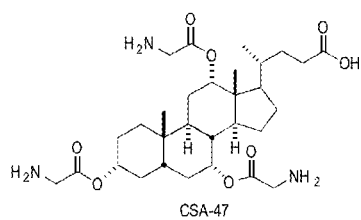
Figure 1A:
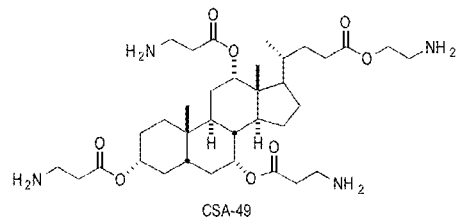
Figure 1A:
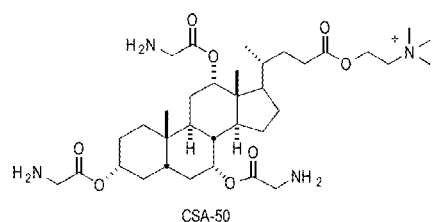
Figure 1A:
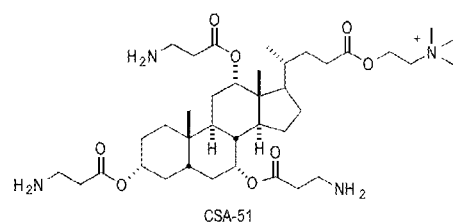
Figure 1A:
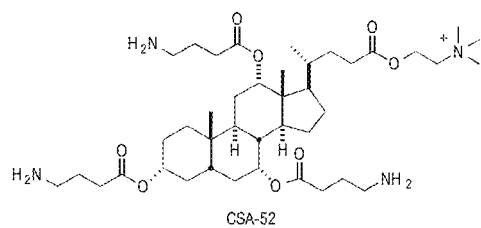
Figure 1A:
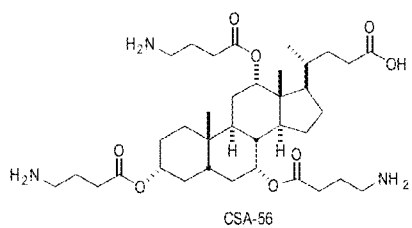
Figure 1A:
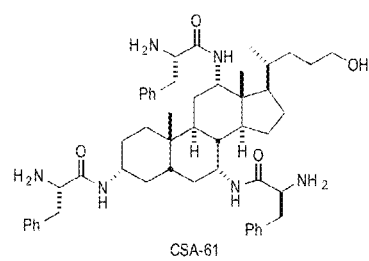
Figure 1A:
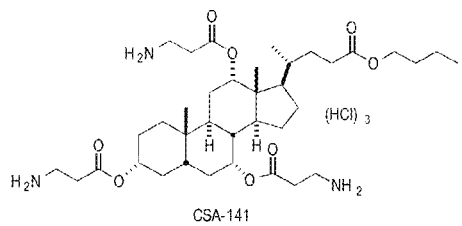
Figure 1A:
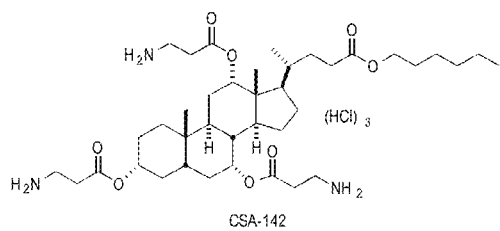
Figure 1A:
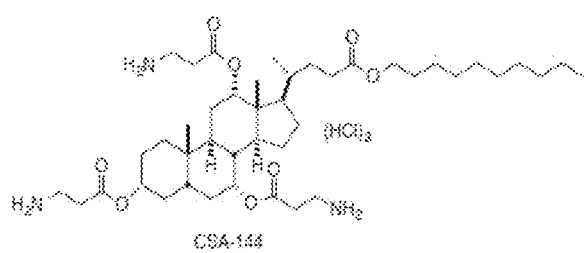
Figure 1A:
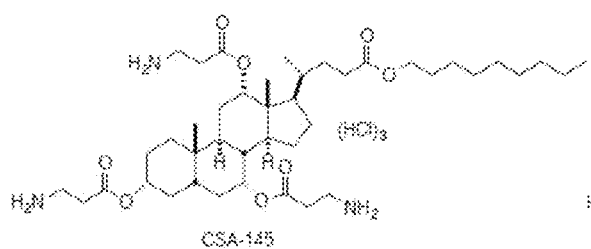
Figure 1A:
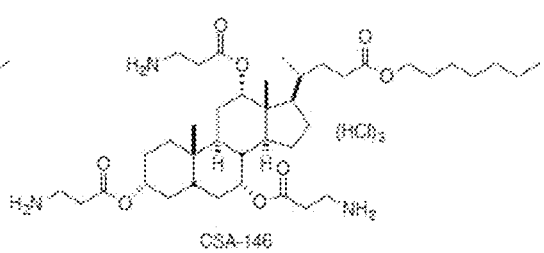

Disclosed herein are methods of treating ciliated tissues using CSA micelle compositions (also referred to herein as "stabilized CSA compositions") that maintain or increase efficacy in killing microbes while reducing or minimizing cytotoxicity to ciliated mammalian cells by encapsulating the CSA compounds in micelles. As used herein, a "micelle" is an aggregate of surfactant molecules dispersed in a liquid colloid. A typical micelle in an aqueous or other polar solution forms an aggregate with the hydrophilic "head" regions in contact with the surrounding solvent. The hydrophobic (e.g., single-tail) regions are sequestered in the micelle center. In some cases, this phase is caused by the packing behavior of single-tailed lipids in a bilayer. This type of micelle is known as a "normal-phase micelle" (e.g., "oil-in-water micelle"). "Inverse micelles" have the hydrophilic head groups at the micelle center, with the tails extending outwardly from the micelle surface (e.g., "waterin-oil micelle"). Micelles can be approximately spherical in shape, although other shapes, such as ellipsoids, cylinders, and bilayers, are also possible. The shape and size of a micelle are a function of the molecular geometry of its surfactant molecules and solution conditions such as surfactant concentration, temperature, pH, and ionic strength. The process of forming micelles is known as "micellization".

It has now been found that negative effects caused by CSA agglomeration and instability can be offset by forming micelles within the solvent or carrier liquid using a suitable amphiphilic compound or composition that is able to encapsulate the CSA molecules and reduce or prevent agglomeration within the composition. Examples of suitable micelle-forming amphiphilic compounds or compositions include one or more surfactants having separate hydrophobic and hydrophilic regions, including poloxamers such as the poloxamer sold under the trade name PLURONIC F127. Because CSA molecules are themselves amphiphilic and often behave as surfactants, the realization that utilizing a different amphiphilic compound or surfactant within the solvent or carrier liquid to form micelles that can encapsulate the CSA molecules and reduce or prevent agglomeration within the composition was not previously recognized nor readily apparent.

Further, it has now been found that combinations of a poloxamer surfactant and CSA compounds decreases cytotoxicity to ciliated cells without substantially impairing antibacterial and antifungal activity, including antibiofilm activity. Without being bound to a particular theory, it is believed that the mechanism of decreased toxicity to ciliated cells is due to transient encapsulation of CSAs in micelles formed by the poloxamer. While ensconced in micelles, CSAs are less prone to associate with host membranes, yet retain high affinity to microbial membranes. In this manner, the micelles act to amplify the membrane selectivity of the CSA compounds in favor of interaction with microbial cell membranes.

II. CSA Micelle Treatment Compositions

In some embodiments, a treatment composition used to treat ciliated tissue includes (1) a carrier; (2) CSA compound; and (3) a poloxamer. The CSA compound is preferably included at a concentration of at least about 5 μg/ml. Particularly effective results have been shown when treating ciliated lung and trachea epithelial tissue using a concentration of about 50 μg/ml to about 100 μg/ml. Such concentrations were able to provide effective antimicrobial activity against bacterial and fungal biofilms without significantly disrupting ciliary function. In other implementations, higher or lower CSA concentrations may be suitable. For example, in some circumstances the CSA composition may be included at a concentration of up to about 150 μg/ml or even 200 μg/ml without significantly disrupting the ciliary function of treated tissue. In other implementations, a CSA concentration as low as 10 μg/ml, 20 μg/ml, 30 μg/ml, or 40 μg/ml may be sufficient to treat a particular infection.

Exemplary carriers include, but are not limited to, water (e.g., distilled water), aqueous solutions, sugar solutions, saline solutions, lactated Ringer's Solution, alcohol (e.g., ethanol), aqueous alcohol solutions, aqueous acid solutions (e.g., organic and/or inorganic acid solutions, such as acetic acid, lactic acid, and the like), aqueous acid salt solutions, glycerine, propylene glycol, 1,3-propanediol, polypropylene glycol, and polyethylene glycol. Particularly preferred carriers include compositions known in the art which are suitable for administration via inhalation and/or suitable for use in conjunction with a nebulizer.

The poloxamer may be included at a concentration of about 0.5% to about 20%, or about 0.75% to about 15%, about 1% to about 10% by weight of the treatment composition, or any range including any of two the foregoing values. At high CSA concentrations of 100 μg/ml, a treatment composition with a poloxamer concentration of 5% was shown to be no different than the control in its effects on ciliary activity. Treatment compositions with lower poloxamer concentrations also exhibited significant reductions in ciliary disruption relative to a treatment composition omitting poloxamer.

The concentration of poloxamer utilized may be determined according to protective effects desired or required in the treatment composition based on the concentration of CSA compound included, with higher concentrations of CSA corresponding to higher concentrations of poloxamer. The poloxamer may be included in an amount proportional to the amount of CSA compound. For example, the poloxamer may be included in an amount, by weight, that is about 100 to 1000 times, or about 250 to 750 times, or about 500 times the amount of CSA compound, by weight. Treatment compositions that include the poloxamer and the CSA compound in these proportioned ratios can effectively balance the need to kill infecting microbes without significantly harming ciliary function.

An exemplary formula of a poloxamer is shown in Formula P below.

Formula P

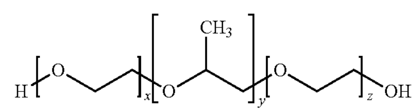

The poloxamer includes a central hydrophobic chain of polyoxypropylene of length y flanked by two hydrophilic chains of polyoxyethylene of lengths x and z. The chain lengths are variable and various poloxomer formulas may be used depending on particular application needs. The lengths x and z typically range from 2 to 130 and the length y typically ranges from 15 to 67.

In a preferred embodiment, the poloxamer is the poloxamer sold under the trade name PLURONIC F-127, (which is similar to and occasionally referred to as poloxamer 407). Using the naming convention in place at the time of filing of this application, coding of PLURONIC copolymers starts with a letter to define its physical form at room temperature (L=liquid, P=paste, F=flake/solid) followed by two or three digits. The first digit (two digits in a three-digit number) in the numerical designation, multiplied by 300, indicates the approximate molecular weight of the hydrophobic polyoxypropylene section; and the last digit multiplied by 10 gives the percentage polyoxyethylene content. Thus, PLURONIC F-127 is a flake/solid at room temperature, has an approximate polyoxypropylene molecular weight of 3,600 g/mol, and is approximately 70% in polyoxyethylene content.

Other poloxamers having similar properties to PLURONIC F-127 may additionally or alternatively be used. For example, a suitable poloxamer may have a polyoxypropylene section with a molecular weight of about 2,500 to 5,500 g/mol, and the polyoxyethylene content may range from about 50% to 90%, or about 60% to 80%.

Beneficially, the treatment of ciliated tissues using CSAs encapsulated in poloxamer micelles allows use of higher concentrations of CSA compound without negatively impacting cilia function. This is particularly beneficial for treating biofilms, as it allows use of CSA concentrations that are high enough to effectively kill the biofilm microbes without causing damage to the cilia that would otherwise occur if the CSA compounds were not provided in combination with a poloxamer.

The preparation of CSA-containing compositions having highly dispersed CSA molecules (e.g., so that less than about 25% of the CSA molecules form agglomerates or particles 1 µm or larger in size) can be dependent on the type of solvent or liquid carrier, micelle-forming agent, and CSA compound(s) and/or the order of mixing the solvent or carrier liquid, micelle-forming agent, and CSA compound(s). In some cases, as will be explained below, the CSA compound(s) can be initially dissolved or dispersed in a suitable solvent or liquid carrier, followed by addition of one or more micelle-forming agents to form micelles that encapsulate at least a portion of the CSA molecules and prevent or reduce agglomeration. In other cases, the CSA compound(s) can be blended or dispersed with one or more micelle-forming agents to form an intermediate mixture, which is thereafter added to a suitable solvent or carrier liquid. The relative hydrophilicity and hydrophobicity of the various components may affect the order of mixing to yield a desired CSA-containing composition.

According to some embodiments, at least about 75%, 85%, 90%, or 95% of the CSA molecules within CSA-containing compositions disclosed herein are in the form of individually sequestered molecules or particles less than 1 µm in size. In some embodiments at least about 75%, 85%, 90%, or 95% of the CSA molecules are in the form of individually sequestered molecules or particles less than 500 nm in size. In some embodiments at least about 75%, 85%, 90%, or 95% of the CSA molecules are in the form of individually sequestered molecules or particles less than 100 nm in size. In some cases it may be useful to consider CSA particles less than 100 nm in size to constitute individually sequestered CSA molecules within micelles.

In some embodiments, less than about 25%, 15%, 10%, or 5% of the CSA molecules form agglomerates or particles larger than about 1 µm in size. In some embodiments, less than about 25%, 15%, 10%, or 5% of the CSA molecules form agglomerates larger than about 500 µm in size. In some embodiments, less than about 25%, 15%, 10%, or 5% of the CSA molecules form agglomerates larger than about 100 µm in size. In some cases it may be desirable to minimize or eliminate CSA agglomerates in order to maximize efficacy in killing microbes and minimize cytotoxicity to mammalian cells.

The particle size distribution of the CSA compounds can be determined using any known particle size analyzer or analysis method. Examples include sieving, optical or electron microscope analysis, laser diffraction, x-ray diffraction, sedimentation, elutriation, microscope counting, Coulter counter, and Dynamic Light Scattering.

III. Methods of Treating Ciliated Tissues

The CSA micelle treatment compositions described herein may be utilized to treat ciliated tissue. The treatment compositions are particularly beneficial for treating ciliated tissue infected with a microbial biofilm or at risk of infection with a microbial biofilm. In one embodiment, a method of treating ciliated tissue comprises: (1) providing a treatment composition as described herein having a CSA compound, a poloxamer, and a carrier; (2) administering the treatment composition to ciliated tissue of a subject in need thereof; and (3) the treatment composition killing microbes associated with the ciliated tissue without significantly disrupting ciliary function.

In some embodiments, the microbes are part of a biofilm, and the treatment composition is effective in eliminating the biofilm infection. The ciliated tissue may include tissues of the upper respiratory tract, sinuses, lungs, trachea, fallopian tubes, uterus, central portion of spinal cord (ependyma), or other ciliated tissues. In some embodiments, the treatment composition is coated onto medical devices that are intended to come into contact with ciliated tissue, such as respiratory tract implants, endotracheal tubes, intrauterine devices, and the like.

The treatment composition may be administered using any suitable administration route. In implementations where the composition is intended to treat ciliated tissues of the respiratory system, the treatment composition is preferably administered via inhalation. In other embodiments, CSA compositions can be administered by other routes, such as direct application, irrigation, lavage, injection, infusion, and the like.

Exemplary carriers for nasal or pulmonary aerosol inhalation administration include solutions in saline which can contain, for example, benzyl alcohol or other suitable preservatives, absorption promoters to enhance bioavailability, and/or other solubilizing or wetting or dispersing agents. Such agents may include glycerin, a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate). Carriers may include polysaccharides and polysaccharide-like compounds (e.g. dextran sulfate), and glycoaminoglycans and glycosaminoglycan-like compounds (e.g., hyaluronic acid), for example. In some embodiments, the carrier may be a solid and the treatment composition may be formulated as a dry powder (e.g., for administering with dry powder inhalers).

Exemplary aerosols useful for nasal and/or inhalation administration can include a vaporizable propellant, such as low molecular weight hydrofluorocarbons or hydrocarbons that are liquid when constrained in a suitable container and are biocompatible and non-irritating. Ingredients such as water, alcohol, propylene glycol, and polyethylene glycols can be additionally included. Other embodiments, also useful for nasal and/or inhalation administration, may be provided as sprays rather than an aerosol propellant. Such spray formulation may be provided as a solution, suspension, or emulsion capable of forming a fine mist for administration, and in some embodiments, may include saline and/or be isotonic.

The term "without significantly disrupting ciliary activity" and similar terms, as used herein, means that treated ciliated tissues are able to maintain clearance and/or sweeping function (e.g., to clear mucous) with no more than about a 25% reduction, 20% reduction, 15% reduction, 10% reduction, or 5% reduction in clearance speed or in an amount of substance cleared. Some implementations may result in no detectable levels of ciliary impairment or reduction in clearance speed or clearance amounts. Such clearance properties can be determined, for example, using standard bead clearance assays.

CSA compositions can be administered at any desired frequency as a single bolus or multiple dose e.g., one, two, three, four, five, or more times hourly, daily, weekly, monthly, or annually or between about 1 to 10 days, weeks, months, or for as long as appropriate. Exemplary frequencies are typically from 1-7 times, 1-5 times, 1-3 times, 2-times or once, daily, weekly or monthly. Timing of contact, administration ex vivo or in vivo delivery can be dictated by the infection, pathogenesis, symptom, pathology or adverse side effect to be treated. For example, an amount can be administered to the subject substantially contemporaneously with, or within about 1-60 minutes or hours of the onset of a symptom or adverse side effect, pathogenesis, or vaccination.

Doses may vary depending upon whether the treatment is therapeutic or prophylactic, the onset, progression, severity, frequency, duration, probability of or susceptibility of the symptom, the type pathogenesis to which treatment is directed, clinical endpoint desired, previous, simultaneous or subsequent treatments, general health, age, gender or race of the subject, bioavailability, potential adverse systemic, regional or local side effects, the presence of other disorders or diseases in the subject, and other factors that will be appreciated by the skilled artisan (e.g., medical or familial history). Dose amount, frequency or duration may be increased or reduced, as indicated by the clinical outcome desired, status of the infection, symptom or pathology, any adverse side effects of the treatment or therapy. The skilled artisan will appreciate the factors that may influence the dosage, frequency and timing required to provide an amount sufficient or effective for providing a prophylactic or therapeutic effect or benefit. The exact dosage will be determined by the practitioner, in light of factors related to the subject that requires treatment. Dosage and administration are adjusted to provide sufficient levels of the active agent(s) or to maintain the desired effect. It will be appreciated that treatment as described herein includes preventing a disease, ameliorating symptoms, slowing disease progression, reversing damage, or curing a disease.

The dosage may range broadly, depending upon the desired effects, the therapeutic indication, and the mode of administration. Alternatively, dosages may be based and calculated upon the surface area of the patient, as understood by those of skill in the art. Although the exact dosage will be determined on a drug-by-drug basis, some generalizations regarding the dosage can be made. In some embodiments, the dosage regimen for local or systemic delivery (based on the weight of the subject) may be about 1 µg/g, 5 µg/g, 10 µg/g, 50 µg/g, 100 µg/g, 200 µg/g, 500 µg/g, 750 µg/g, 1000 µg/g, or less than any of the aforementioned numbers, or a range bounded by any two of the aforementioned numbers. In some embodiments, between about 0.001 mg to about 3000 mg of the active ingredient is delivered is administered locally or systemically. In some embodiments, about 5-15 mg of active ingredient is administered locally or systemically. In other embodiments, about 0.001 mg, 0.01 mg, 0.1 mg, 1 mg, 5 mg, 10 mg, 15 mg, 25 mg, 50 mg, 100 mg, 500 mg, 1000 mg, or less than any of the aforementioned numbers, or a range bounded by any two of the aforementioned numbers is administered locally or systemically.

Additional information regarding the use of CSA compounds to treat lung diseases is disclosed in U.S. Patent Publication No. 2015/0110767, which is incorporated herein by reference.

IV. Manufacture of CSA Micelle Compositions

One exemplary method for forming stabilized CSA compositions includes the steps of: (1) initially dissolving or dispersing one or more CSA compounds in an appropriate solvent, such as ethanol, which may not by itself be the desired carrier liquid in the final composition, to form a stock CSA composition; (2) separately preparing a micelle-forming composition by mixing one or more micelle-forming agents with an appropriate liquid carrier or solvent to form a micelle-forming composition that contains or will later contain micelles suitable for encapsulating CSA compounds; (3) mixing the stock CSA composition with the micelle-forming composition; (4) causing or allowing micelles to encapsulate and stabilize at least a portion of the CSA compounds in the composition; (5) sonicating one or more of the compositions obtained in steps (1) to (4); and (6) optionally adding a solvent, other liquid carrier component, additional micelle-forming agent, additional CSA compound, or other component to the composition(s) obtained in any of steps (1) to (4).

An alternative method for forming stabilized CSA compositions includes the steps of: (1) initially mixing one or more CSA compounds with one or more micelle-forming agents to form an intermediate stock composition; (2) mixing the intermediate stock composition with an appropriate liquid carrier or solvent; (3) causing or allowing micelles to encapsulate and stabilize at least a portion of the CSA compounds in the composition; (4) sonicating one or more of the compositions obtained in steps (1) to (3); and (5) optionally adding a solvent, other liquid carrier component, additional micelle-forming agent, additional CSA compound, or other component to the composition(s) obtained in any of steps (1) to (3).

Yet another alternative method for forming stabilized CSA compositions includes the steps of: (1) initially mixing one or more CSA compounds with a first micelle-forming agent to form a CSA stock composition; (2) separately mixing a second micelle-forming agent with an appropriate liquid carrier or solvent to form a micelle-forming stock composition; (3) mixing the CSA stock composition with the micelle-forming stock composition; (4) causing or allowing micelles to encapsulate and stabilize at least a portion of the CSA compounds in the composition; (5) sonicating one or more of the compositions obtained in steps (1) to (4); and (6) optionally adding a solvent, other liquid carrier component, additional micelle-forming agent, additional CSA compound, or other component to the composition(s) obtained in any of steps (1) to (3).

Examples of micelle-forming agents include a wide variety of amphillilic materials that are able to become appropriately aligned when mixed with an appropriate liquid carrier so as to form micelles. It is especially desirable for the micelles so formed to form micelle centers that have an affinity for and are therefore capable of encapsulating one or a small number of CSA molecules in order to reduce or prevent agglomeration and yield stabilized compositions. Some materials that form micelles when mixed with one type of liquid carrier may not form micelles in another liquid carrier or outside of certain concentration ranges. Nevertheless, so long as a material is able to form micelles in at least one type of liquid carrier and/or at certain concentrations, it will be considered to be a "micelle-forming agent".

Examples of micelle-forming agents include, but are not limited to, modified celluloses, modified surfactants, modified non-oxidizing vehicles, and organic acids. More specific examples include modified nonionic hydroxyethyl cellulose, natural polyoxyethylene sorbitol ester, hydroxyethyl cellulose, 2-hydroxyethyl cellulose with molecular weights between 90,000 and 750,000 with a viscosity between 50-500 cps in solutions between 1% and 5% water at temperatures between 20° C. and 25° C., modified aqueous solutions of polysorbate nonionic surfactants, polyoxyethylene sorbitan mono-, di-, and tri-($C_{12}$-$C_{18}$)-alkanoates, poloxamers, which are nonionic triblock copolymers composed of a central hydrophobic chain of polyoxypropylene (poly(propylene oxide)) flanked by two hydrophilic chains of polyoxyethylene (poly(ethylene oxide)), examples of which are sold under the tradename PLURONIC, a non-limiting example of which includes PLURONIC F-127, polyoxyethylene(20) sorbitan trioleate sold under the tradename TWEEN™ 85, polyoxyethylene(20) sorbitan monooleate sold under the tradename TWEEN™ 80, polyoxyethylene(20) sorbitan monostearate sold under the tradename TWEEN™ 60, polyoxyethylene (20) sorbitan monopalmitate sold under the tradename TWEEN™ 40, and polyoxyethylene(20) sorbitan monolaurate sold under the tradename TWEEN™ 20, hydroxymethyl cellulose, ethyl cellulose, methyl cellulose (e.g., Methocel), hydroxypropyl cellulose, carboxymethyl cellulose, emulsifying waxes, alkyl triammonium methosulfate, ceteraryloctanoate, polyols, and polyalkylene glycols having alkylene moieties containing about 2-3 carbon atoms.

Additional information regarding the manufacture of CSA compounds and particles dispersed using micelles is disclosed in U.S. Patent Publication No. 2015/0258121, which is incorporated herein by reference.

V. Additional Details Relating to CSA Compounds

CSA compounds are synthetically produced small molecule chemical compounds that include a sterol backbone having various charged groups (e.g., amine, guanidine, and/or other groups capable of exhibiting cationic properties under biological conditions) attached to the backbone. The backbone can be used to orient the cationic groups on one face, or plane, of the sterol backbone. In general, "CSA compound" refers to the class, type, or structure, while "CSA molecule" refers to an actual CSA molecule.

CSAs are cationic and amphiphilic, based upon the functional groups attached to the backbone. They are facially amphiphilic with a hydrophobic face and a polycationic face. Without wishing to be bound to any particular theory, it is theorized that the CSA compounds described herein act as anti-microbial agents (e.g., anti-bacterials, anti-fungals, and anti-virals) by binding to the cellular membrane of bacteria and other microbes and inserting into the cell membrane, forming a pore that allows the leakage of ions and cytoplasmic materials that are critical to the microbe's survival, thereby leading to the death of the affected microbe.

An example of a CSA compound is shown below as Formula I. As will be discussed in greater detail below, the R groups of Formula I can have a variety of different functionalities, thus providing a given ceragenin compound with specific, different properties. In addition, as will be appreciated by those of skill in the art, the sterol backbone can be formed of 5-member and/or 6-member rings, so that p, q, m, and n may independently be 1 (providing a 6-member ring) or 0 (providing a 5-member ring).

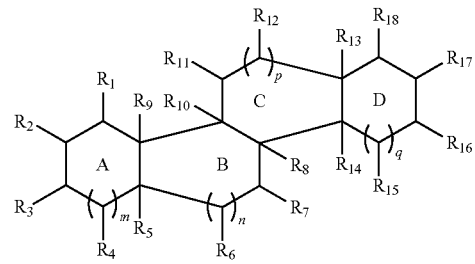

Typically, the CSAs of Formula I are of two types: (1) CSAs having cationic groups linked to the sterol backbone with hydrolysable linkages and (2) CSAs having cationic groups linked to the sterol backbone with non-hydrolysable linkages. For example, one type of hydrolysable linkage is an ester linkage, and one type of non-hydrolysable linkage is an ether linkage. CSAs of the first type can be "inactivated" by hydrolysis of the linkages coupling the cationic groups to the sterol backbone, whereas CSAs of the second type are more resistant to degradation and inactivation.

Figure 1B:
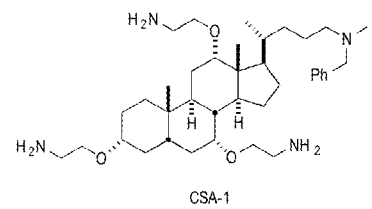
FIG. 1B illustrates exemplary non-hydrolysable CSA compounds.
Figure 1B:
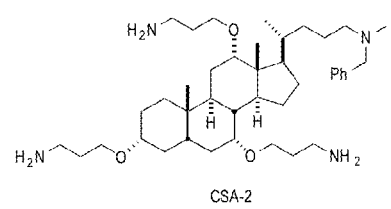
Figure 1B:
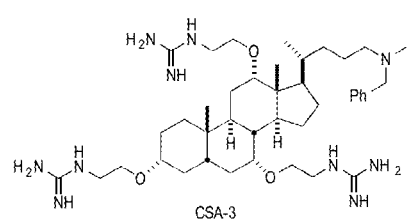
Figure 1B:
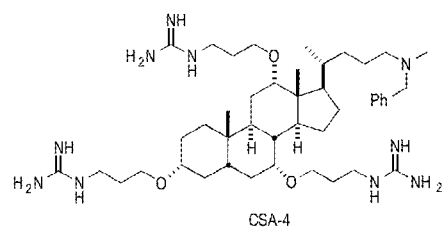
Figure 1B:
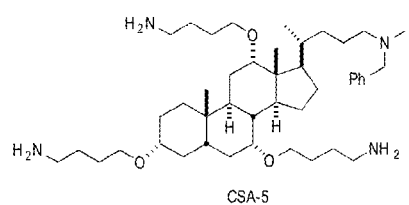
Figure 1B:
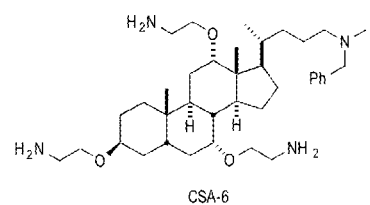
Figure 1B:
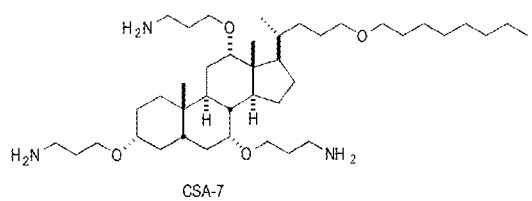
Figure 1B:
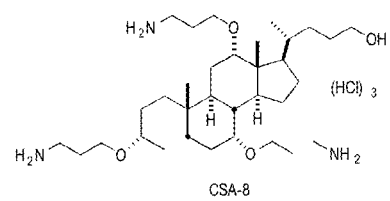
Figure 1B:
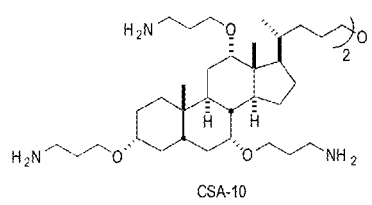
Figure 1B:
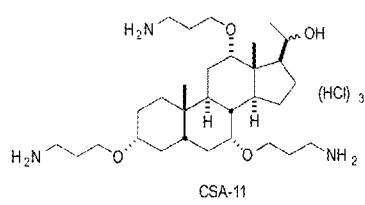
Figure 1B:
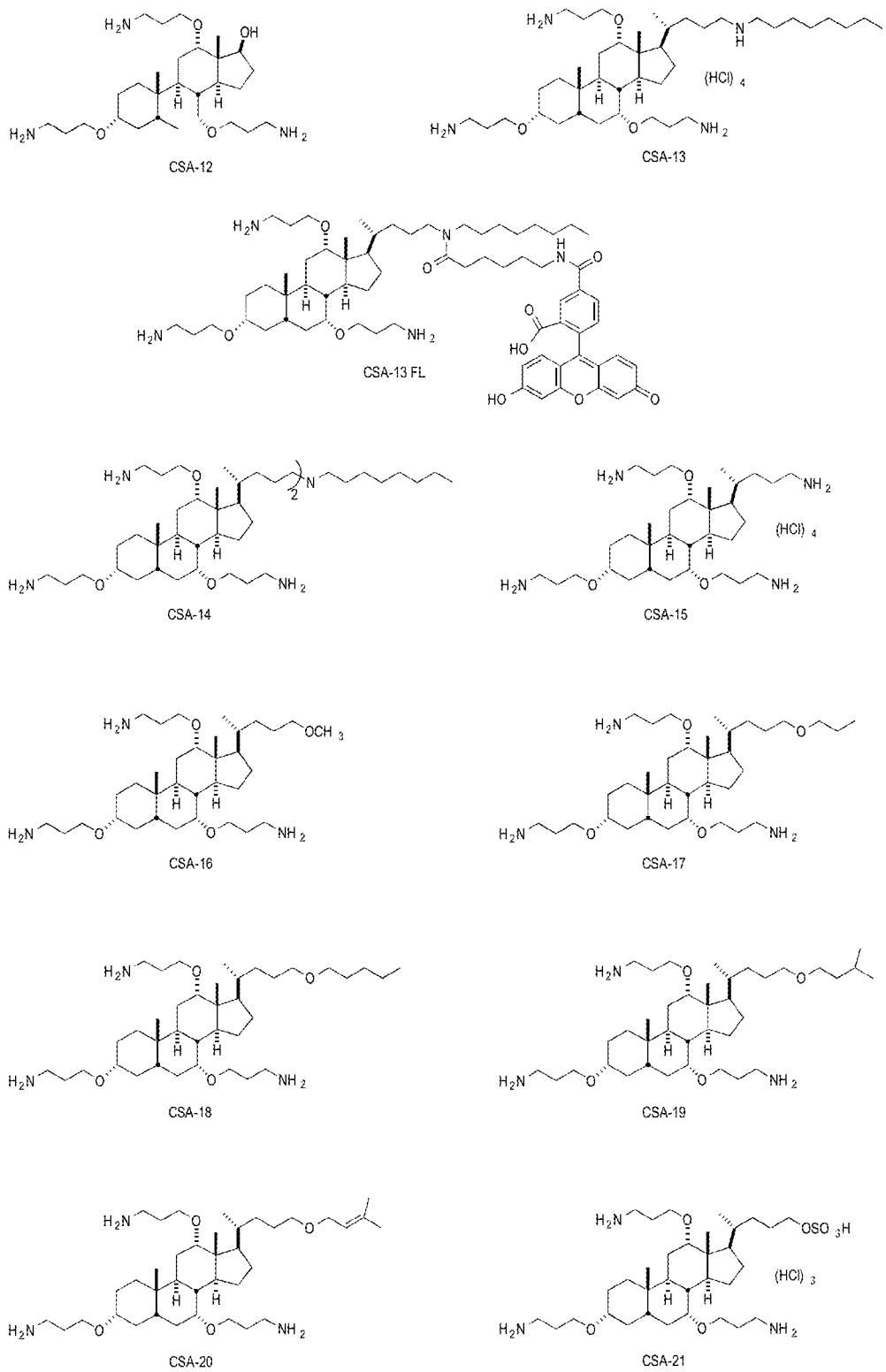
Figure 1B:
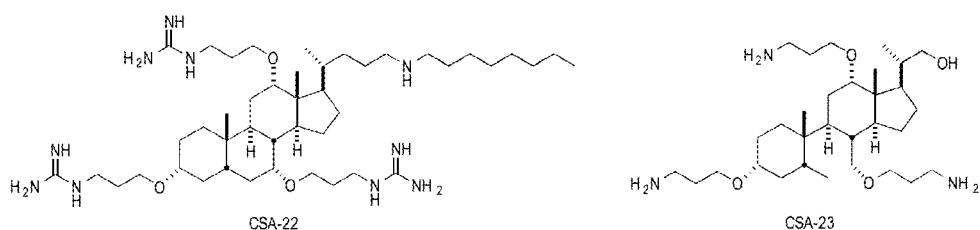
Figure 1B:
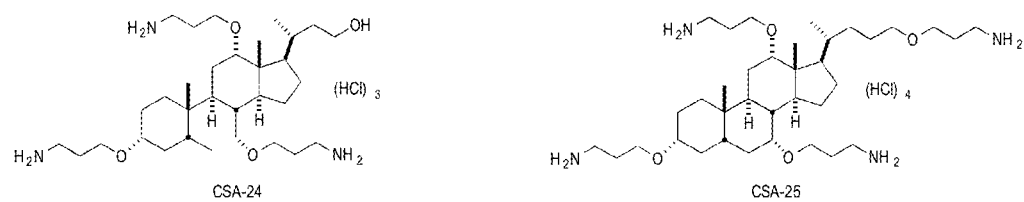
Figure 1B:
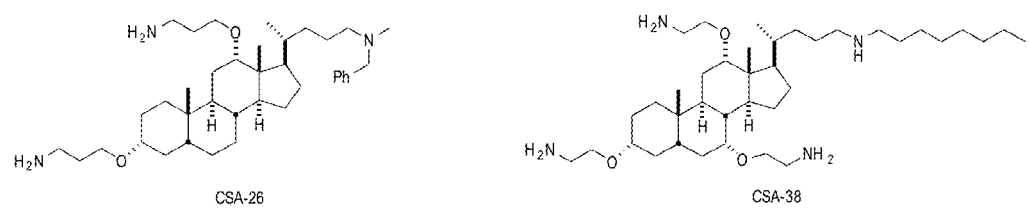
Figure 1B:
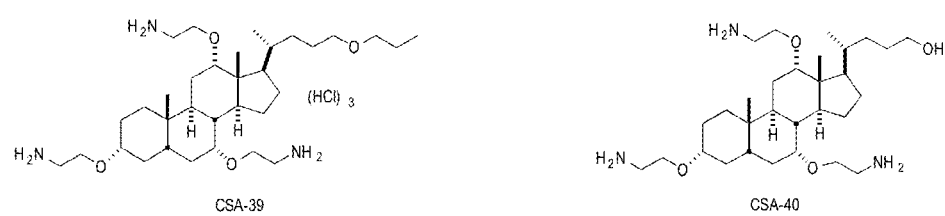
Figure 1B:
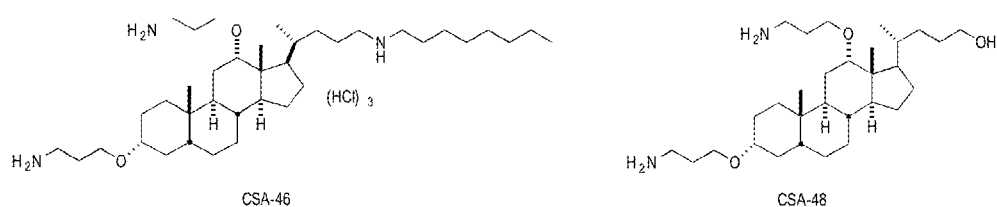
Figure 1B:
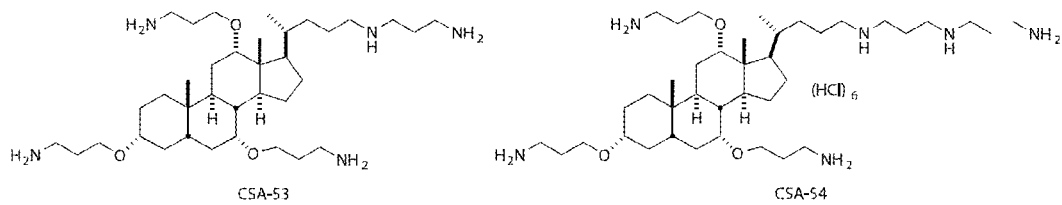
Figure 1B:
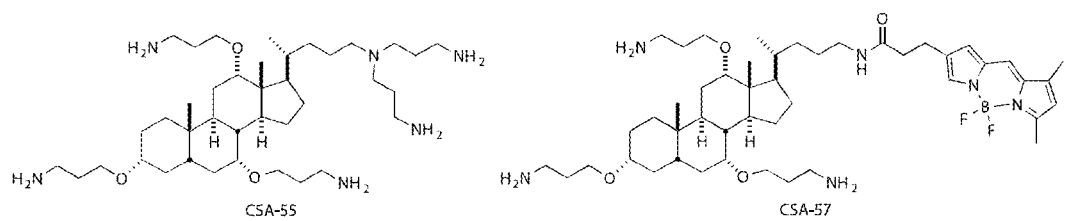
Figure 1B:
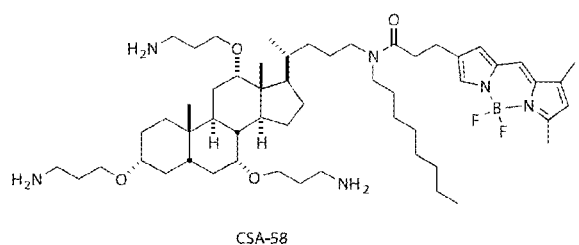
Figure 1B:
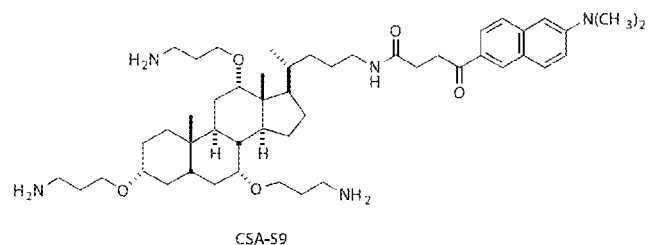
Figure 1B:
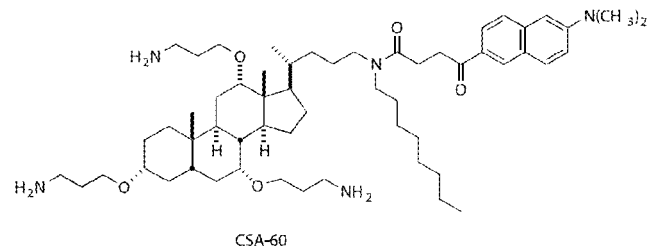
Figure 1B:
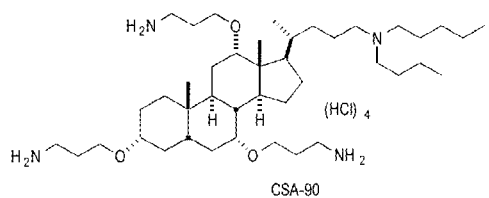
Figure 1B:
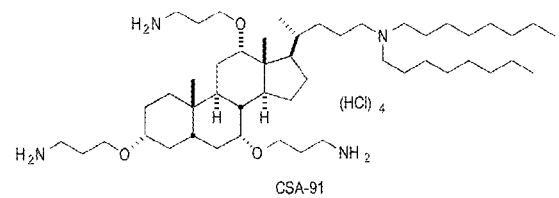
Figure 1B:
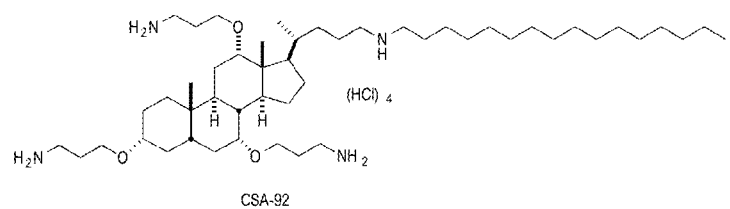
Figure 1B:
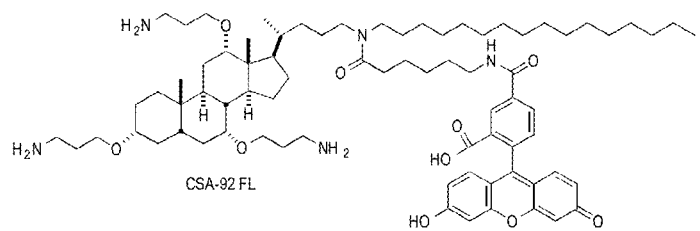
Figure 1B:
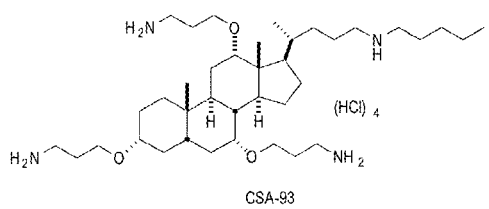
Figure 1B:
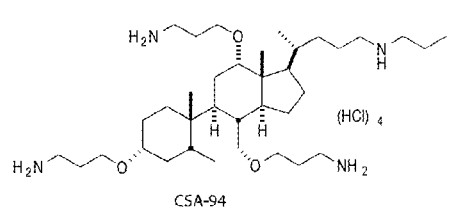
Figure 1B:
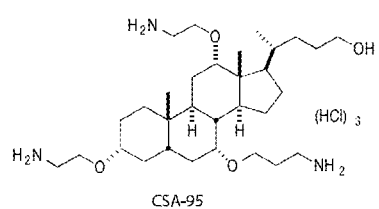
Figure 1B:
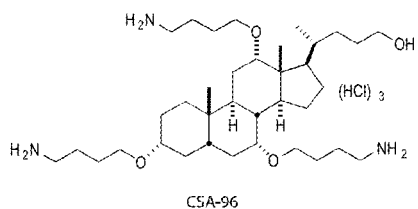
Figure 1B:
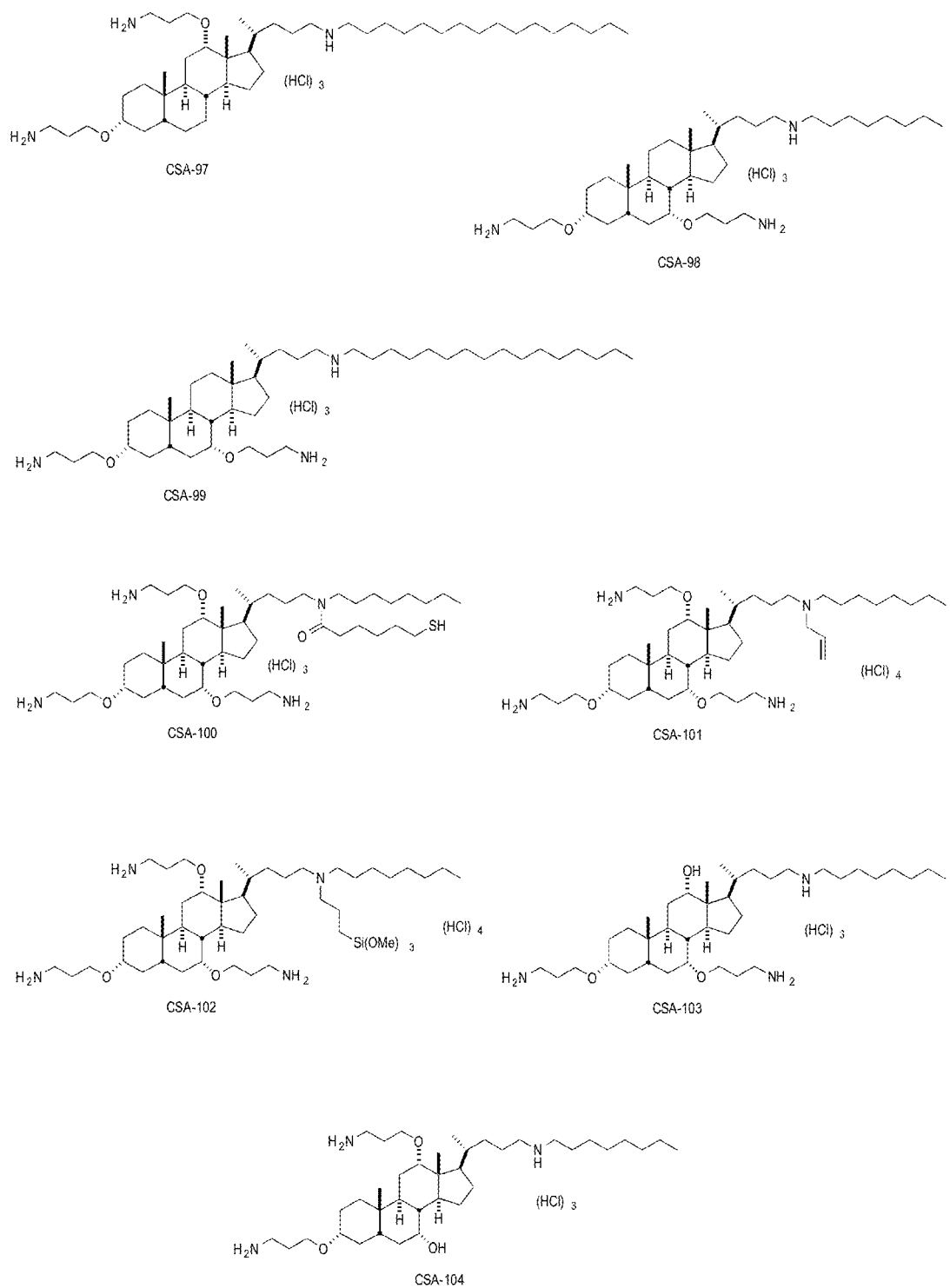
Figure 1B:
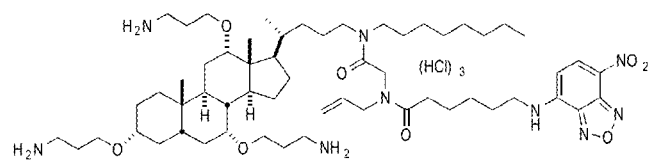
Figure 1B:
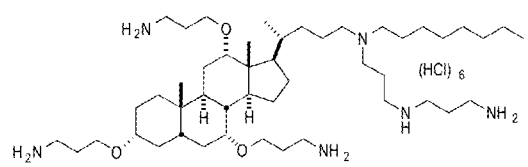
Figure 1B:
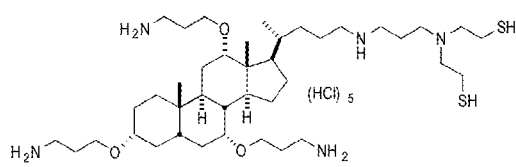
Figure 1B:
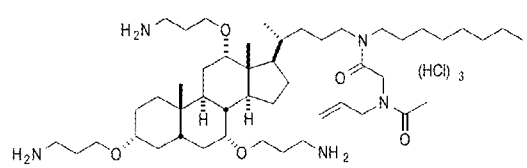
Figure 1B:
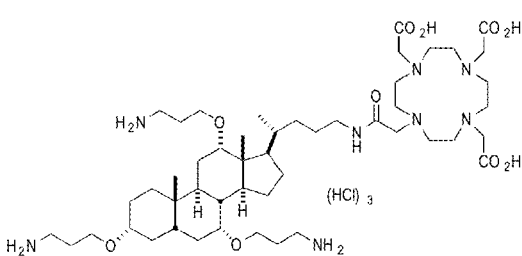
Figure 1B:
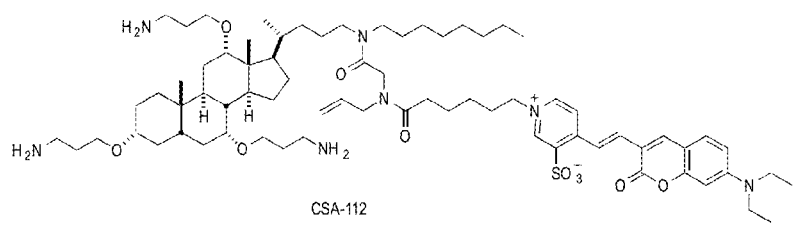
Figure 1B:
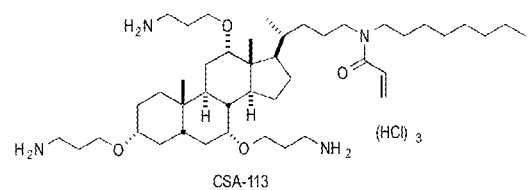
Figure 1B:
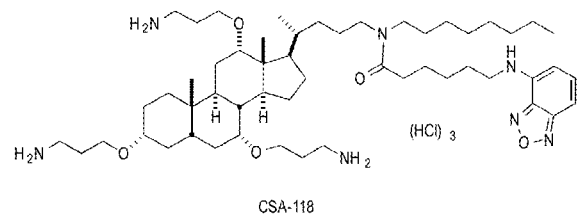
Figure 1B:
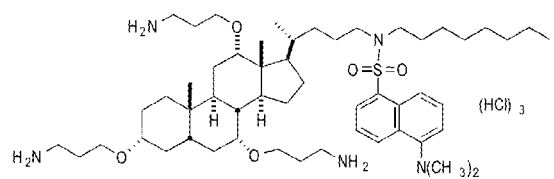
Figure 1B:
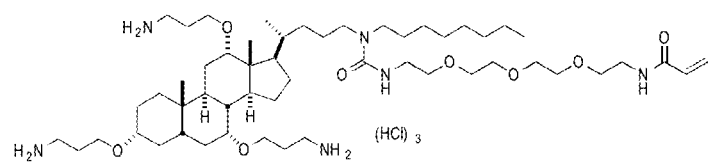
Figure 1B:
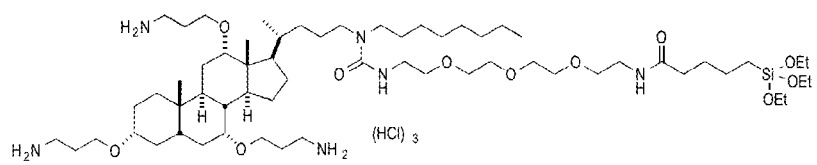
Figure 1B:
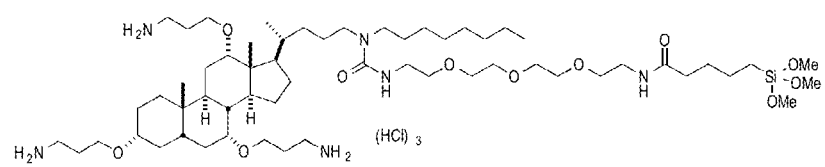
Figure 1B:
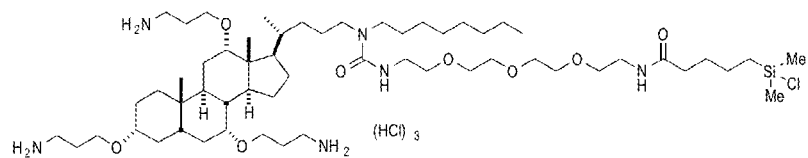
Figure 1B:
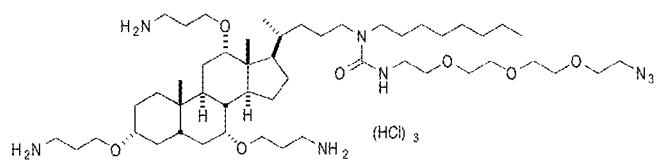
Figure 1B:
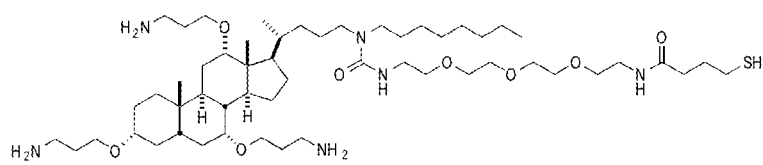
Figure 1B:
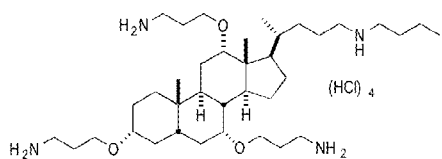
Figure 1B:
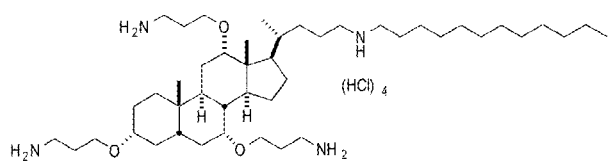
Figure 1B:
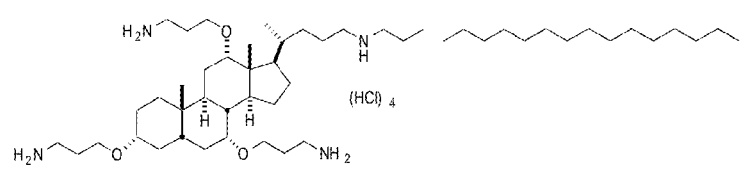
Figure 1B:
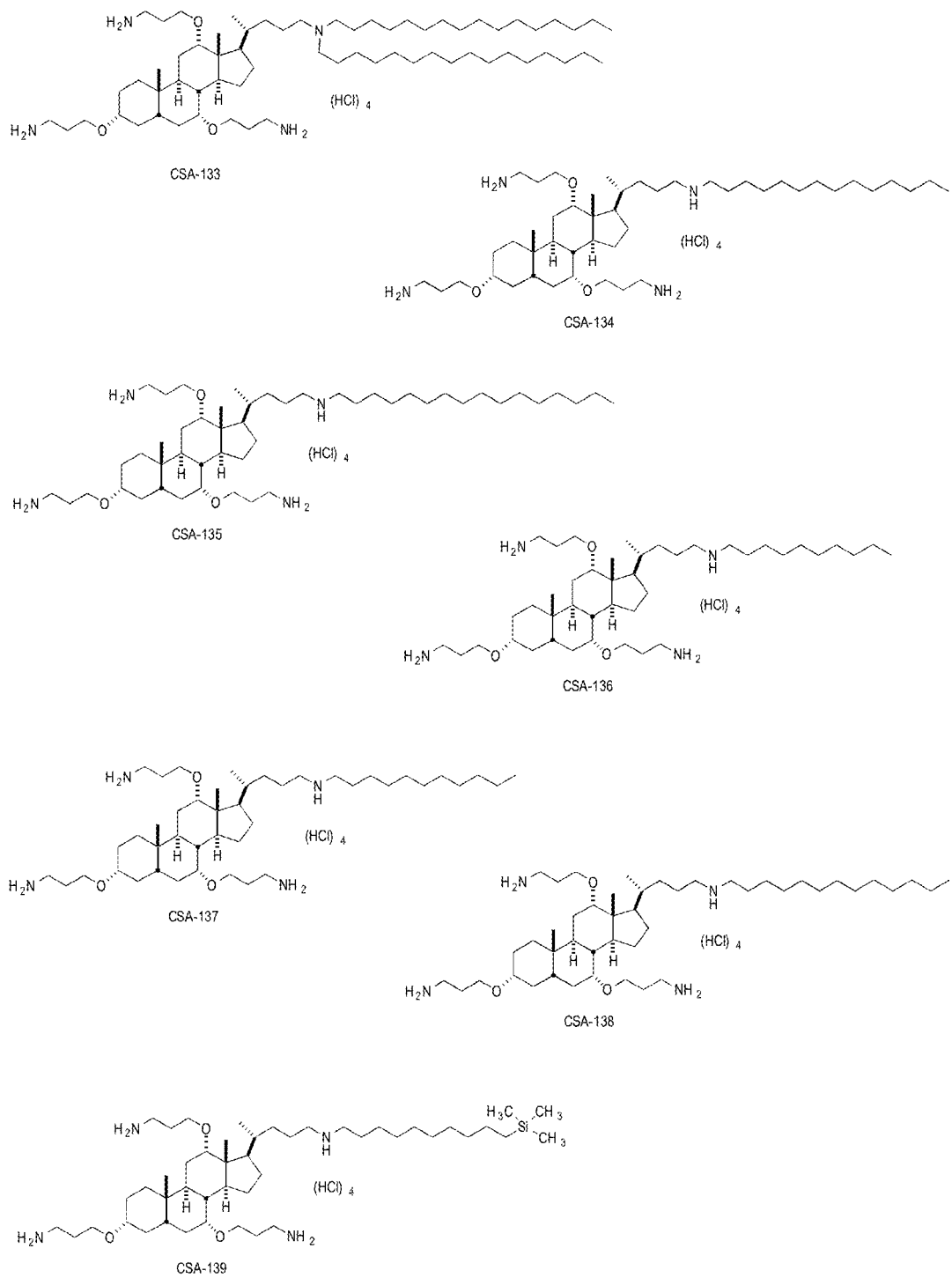
Figure 1C:
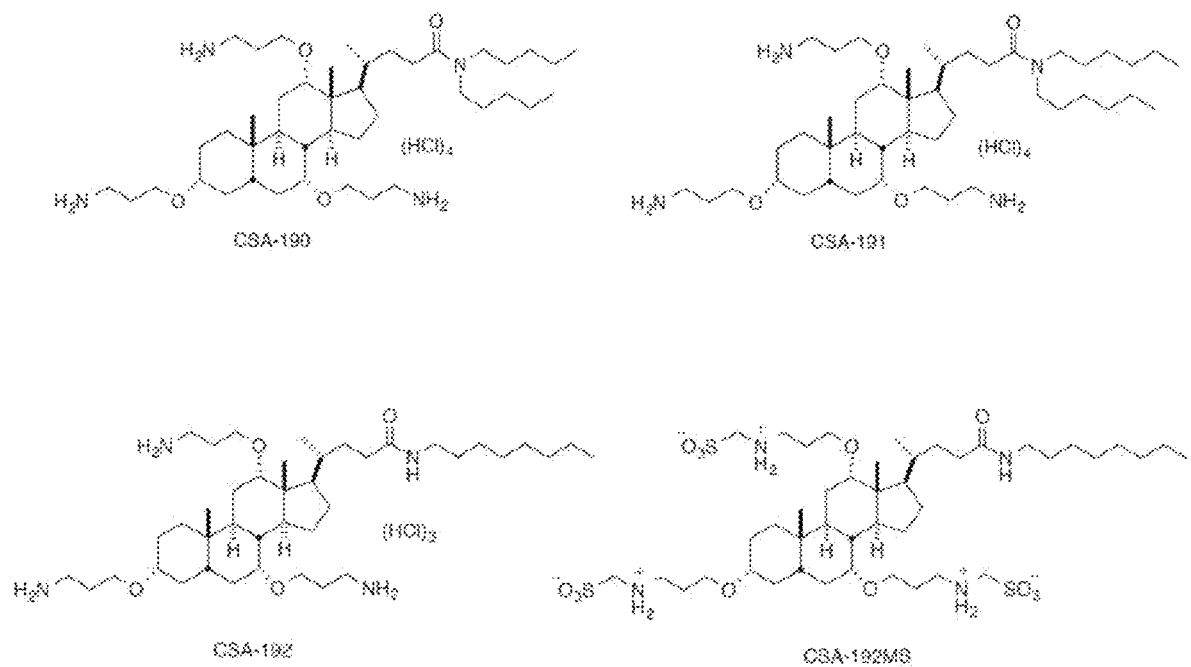
FIG. 1C illustrates exemplary CSA compounds with amido linkages at the R18 position.

A number of examples of compounds of Formula I that may be used in the embodiments described herein are illustrated in FIGS. 1A-1C. Examples of CSAs with non-hydrolysable linkages include, but are not limited to, CSA-1, CSA-26, CSA-38, CSA-40, CSA-46, CSA-48, CSA-53, CSA-55, CSA-57, CSA-60, CSA-90, CSA-107, CSA-109, CSA-110, CSA-112, CSA-113, CSA-118, CSA-124, CSA-130, CSA-131, CSA-139, CSA-190, CSA-191 and CSA-192. Examples of CSAs with hydrolysable linkages include, but are not limited to CSA-27, CSA-28, CSA-29, CSA-30, CSA-31, CSA-32, CSA-33, CSA-34, CSA-35, CSA-36, CSA-37, CSA-41, CSA-42, CSA-43, CSA-44, CSA-45, CSA-47, CSA-49, CSA-50, CSA-51, CSA-52, CSA-56, CSA-61, CSA-141, CSA-142, CSA-144, CSA-145 and CSA-146. Examples of CSA compounds with amide linkages at the $R_{18}$ position include CSA-190, CSA-191, CSA-192, and CSA-192 MS.

In Formula I, at least two of $R_3$, $R_7$, or $R_{12}$ may independently include a cationic moiety attached to the Formula I structure via a hydrolysable (e.g., an ester) or non-hydrolizable (e.g., an ether) linkage. A tail moiety is usually attached to Formula I at $R_{18}$. The tail moiety may be charged, uncharged, polar, non-polar, hydrophobic, or amphipathic, for example, and can thereby be selected to adjust the properties of the CSA and/or to provide desired characteristics.

The activity of the CSA compounds can be affected by the orientation of the substituent groups attached to the backbone structure. In one embodiment, the substituent groups attached to the backbone structure are oriented on a single face of the CSA compound. Accordingly, each of $R_3$, $R_7$, and $R_{12}$ may be positioned on a single face of Formula I. In addition, $R_{18}$ may also be positioned on the same single face of Formula I.

More specific examples of CSA compounds according to Formula I are shown below in Formulas II and III, wherein Formula III differs from Formula II by omitting $R_{15}$ and the ring carbon to which it is attached. The R groups shown in the Formulae can have a variety of different structures. CSA compounds, and a variety of different R groups, useful in accordance with the present disclosure, are disclosed in U.S. Pat. Nos. 6,350,738, 6,486,148, 6,767,904, 7,598,234, 7,754,705, 8,975,310, and 9,434,759, which are incorporated herein by reference.

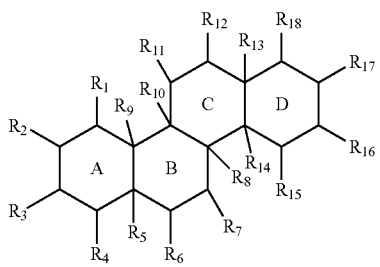

(II)

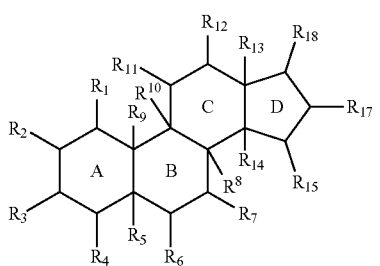

(III)

In some embodiments of Formulas II and III, at least two of $R_3$, $R_7$, and $R_{12}$ may independently include a cationic moiety (e.g., amino or guanidino groups) bonded to the steroid backbone structure via a non-hydrolysable or hydrolysable linkage. For the embodiments of the present disclosure, the linkage is preferably non-hydrolysable under conditions of sterilization and storage, and physiological conditions. Such cationic functional groups (e.g., amino or guanidino groups) may be separated from the backbone by at least one, two, three, four or more atoms.

A tail moiety may be attached to the backbone structures at $R_{18}$. The tail moiety may have variable chain length or size and may be charged, uncharged, polar, non-polar, hydrophobic, amphipathic, and the like. The tail moiety may, for example, be configured to alter the hydrophobicity/hydrophilicity of the ceragenin compound. CSA compounds of the present disclosure having different degrees of hydrophobicity/hydrophilicity may, for example, have different rates of uptake into different target microbes.

The R groups described herein, unless specified otherwise, may be substituted or unsubstituted.

In some embodiments shown by Formulas II and III:

each of fused rings A, B, C, and D may be independently saturated, or may be fully or partially unsaturated, provided that at least two of A, B, C, and D is saturated, wherein rings A, B, C, and D form a ring system. Other ring systems can also be used, e.g., 5-member fused rings and/or compounds with backbones having a combination of 5- and 6-membered rings;

$R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, alkyl, hydroxyalkyl, alkyloxyalkyl, alkylcarboxyalkyl, alkylaminoalkyl, alkylaminoalkylamino, alkylaminoalkylamino-alkylamino, aminoalkyl, aryl, arylaminoalkyl, haloalkyl, alkenyl, alkynyl, oxo, a linking group attached to a second steroid, aminoalkyloxy, aminoalkyloxyalkyl, aminoalkylcarboxy, aminoalkylaminocarbonyl, aminoalkylcarboxamido, di(alkyl)aminoalkyl, $H_2N$—$HC(Q_5)$-$C(O)$—$O$—, $H_2N$—$HC(Q_5)$-$C(O)$—$N(H)$—, azidoalkyloxy, cyanoalkyloxy, P.G.-HN—$HC(Q_5)$-$C(O)$—$O$—, guanidinoalkyloxy, quaternary ammonium alkylcarboxy, and guanidinoalkyl carboxy, where $Q_5$ is a side chain of any amino acid (including a side chain of glycine, i.e., H), and P.G. is an amino protecting group; and $R_5$, $R_8$, $R_9$, $R_{10}$, $R_{13}$, $R_{14}$ and $R_{18}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, alkyl, hydroxyalkyl, alkyloxyalkyl, aminoalkyl, aryl, haloalkyl, alkenyl, alkynyl, oxo, a linking group attached to a second steroid, aminoalkyloxy, aminoalkylcarboxy, aminoalkylaminocarbonyl, di(alkyl)aminoalkyl, $H_2N$—$HC(Q_5)$-$C(O)$—$O$—, $H_2N$—$HC(Q_5)$-$C(O)$—$N(H)$—, azidoalkyloxy, cyanoalkyloxy, P.G.-HN—$HC(Q_5)$-$C(O)$—$O$—, guanidinoalkyloxy, and guanidinoalkyl-carboxy, where $Q_5$ is a side chain of any amino acid, P.G. is an amino protecting group.

In some embodiments, at least one, and sometimes two or three of $R_{1-4}$, $R_6$, $R_7$, $R_{11}$, $R_{12}$, $R_{15}$, $R_{16}$, $R_{17}$, and $R_{18}$ are independently selected from the group consisting of aminoalkyl, aminoalkyloxy, alkylcarboxyalkyl, alkylaminoalkylamino, alkylaminoalkyl-aminoalkylamino, aminoalkylcarboxy, arylaminoalkyl, aminoalkyloxyaminoalkylaminocarbonyl, aminoalkylaminocarbonyl, aminoalkylcarboxyamido, a quaternary ammonium alkylcarboxy, di(alkyl)aminoalkyl, $H_2N$—$HC(Q_5)$-$C(O)$—$O$—, $H_2N$—$HC(Q_5)$-$C(O)$—$N(H)$—, azidoalkyloxy, cyanoalkyloxy, P.G.-HN—$HC(Q_5)$-$C(O)$—$O$—, guanidine-alkyloxy, and guanidinoalkylcarboxy.

In some embodiments, $R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, ($C_1$-$C_{22}$) alkyl, ($C_1$-$C_{22}$) hydroxyalkyl, ($C_1$-$C_{22}$) alkyloxy-($C_1$-$C_{22}$) alkyl, ($C_1$-$C_{22}$) alkylcarboxy-($C_1$-$C_{22}$) alkyl, ($C_1$-$C_{22}$) alkylamino-($C_1$-$C_{22}$) alkyl, ($C_1$-$C_{22}$) alkylamino-($C_1$-$C_{22}$) alkylamino, ($C_1$-$C_{22}$) alkylamino-($C_1$-$C_{22}$) alkylamino-($C_1$-$C_{22}$) alkylamino, ($C_1$-$C_{22}$) aminoalkyl, aryl, arylamino-($C_1$-$C_{22}$) alkyl, ($C_1$-$C_{22}$) haloalkyl, $C_2$-$C_6$ alkenyl, $C_2$-$C_6$ alkynyl, oxo, a linking group attached to a second steroid, ($C_1$-$C_{22}$) aminoalkyloxy, ($C_1$-$C_{22}$) aminoalkyloxy-($C_1$-$C_{22}$) alkyl, ($C_1$-$C_{22}$) aminoalkylcarboxy, ($C_1$-$C_{22}$) aminoalkylaminocarbonyl, ($C_1$-$C_{22}$) aminoalkyl-carboxamido, di($C_1$-$C_{22}$ alkyl)aminoalkyl, $H_2N$—$HC(Q_5)$-$C(O)$—$O$—, $H_2N$—$HC(Q_5)$-$C(O)$—$N(H)$—, ($C_1$-$C_{22}$) azidoalkyloxy, ($C_1$-$C_{22}$) cyanoalkyloxy, P.G.-HN—$HC(Q_5)$-$C(O)$—$O$—, ($C_1$-$C_{22}$) guanidinoalkyloxy, ($C_1$-$C_{22}$) quaternary ammonium alkylcarboxy, and ($C_1$-$C_{22}$) guanidinoalkyl carboxy, where $Q_5$ is a side chain of an amino acid (including a side chain of glycine, i.e., H), and P.G. is an amino protecting group; and $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, ($C_1$-$C_{22}$) alkyl, ($C_1$-$C_{22}$) hydroxyalkyl, ($C_1$-$C_{22}$) alkyloxy-($C_1$-$C_{22}$) alkyl, ($C_1$-$C_{22}$) aminoalkyl, aryl, ($C_1$-$C_{22}$) haloalkyl, ($C_2$-$C_6$) alkenyl, ($C_2$-$C_6$) alkynyl, oxo, a linking group attached to a second steroid, ($C_1$-$C_{22}$) aminoalkyloxy, ($C_1$-$C_{22}$) aminoalkylcarboxy, ($C_1$-$C_{22}$) aminoalkylaminocarbonyl, di($C_1$-$C_{22}$ alkyl)aminoalkyl, $H_2N$—$HC(Q_5)$-$C(O)$—$O$—, $H_2N$—$HC(Q_5)$-$C(O)$—$N(H)$—, ($C_1$-$C_{22}$) azidoalkyloxy, ($C_1$-$C_{22}$) cyanoalkyloxy, P.G.-HN—$HC(Q_5)$-$C(O)$—$O$—, ($C_1$-$C_{22}$) guanidinoalkyloxy, and ($C_1$-$C_{22}$) guanidinoalkylcarboxy, where Q5 is a side chain of any amino acid, and P.G. is an amino protecting group;

provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of ($C_1$-$C_{22}$) aminoalkyl, ($C_1$-$C_{22}$) aminoalkyloxy, ($C_1$-$C_{22}$) alkylcarboxy-($C_1$-$C_{22}$) alkyl, ($C_1$-$C_{22}$)

alkylamino-($C_1$-$C_{22}$) alkylamino, ($C_1$-$C_{22}$) alkylamino-($C_1$-$C_{22}$) alkylamino ($C_1$-$C_{22}$) alkylamino, ($C_1$-$C_{22}$) aminoalkylcarboxy, arylamino ($C_1$-$C_{22}$) alkyl, ($C_1$-$C_{22}$) aminoalkyloxy ($C_1$-$C_{22}$) aminoalkylaminocarbonyl, ($C_1$-$C_{22}$) aminoalkylaminocarbonyl, ($C_1$-$C_{22}$) aminoalkylcarboxyamido, ($C_1$-$C_{22}$) quaternary ammonium alkylcarboxy, di($C_1$-$C_{22}$ alkyl) aminoalkyl, $H_2N$—HC($Q_5$)-C(O)—O—, $H_2N$—HC($Q_5$)-C(O)—N(H)—, ($C_1$-$C_{22}$) azidoalkyloxy, ($C_1$-$C_{22}$) cyanoalkyloxy, P.G.-HN—HC($Q_5$)-C(O)—O—, ($C_1$-$C_{22}$) guanidinoalkyloxy, and ($C_1$-$C_{22}$) guanidinoalkylcarboxy.

In some embodiments, $R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, ($C_1$-$C_{18}$) alkyl, ($C_1$-$C_{18}$) hydroxyalkyl, ($C_1$-$C_{18}$) alkyloxy-($C_1$-$C_{18}$) alkyl, ($C_1$-$C_{18}$) alkylcarboxy-($C_1$-$C_{18}$) alkyl, ($C_1$-$C_{18}$) alkylamino-($C_1$-$C_{18}$) alkyl, ($C_1$-$C_{18}$) alkylamino-($C_1$-$C_{18}$) alkylamino, ($C_1$-$C_{18}$) alkylamino-($C_1$-$C_{18}$) alkylamino-($C_1$-$C_{18}$) alkylamino, ($C_1$-$C_{18}$) aminoalkyl, aryl, arylamino-($C_1$-$C_{18}$) alkyl, oxo, ($C_1$-$C_{18}$) aminoalkyloxy, ($C_1$-$C_{18}$) aminoalkyloxy-($C_1$-$C_{18}$) alkyl, ($C_1$-$C_{18}$) aminoalkylcarboxy, ($C_1$-$C_{18}$) aminoalkylaminocarbonyl, ($C_1$-$C_{18}$) aminoalkyl-carboxamido, di($C_1$-$C_{18}$ alkyl)aminoalkyl, ($C_1$-$C_{18}$) guanidinoalkyloxy, ($C_1$-$C_{18}$) quaternary ammonium alkylcarboxy, and ($C_1$-$C_{18}$) guanidinoalkyl carboxy; and $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, ($C_1$-$C_{18}$) alkyl, ($C_1$-$C_{18}$) hydroxyalkyl, ($C_1$-$C_{18}$) alkyloxy-($C_1$-$C_{18}$) alkyl, ($C_1$-$C_{18}$) alkylcarboxy-($C_1$-$C_{18}$) alkyl, ($C_1$-$C_{18}$) alkylamino-($C_1$-$C_{18}$)alkyl, ($C_1$-$C_{18}$) alkylamino-($C_1$-$C_{18}$) alkylamino, ($C_1$-$C_{18}$) alkylamino-($C_1$-$C_{18}$) alkylamino-($C_1$-$C_{18}$) alkylamino, ($C_1$-$C_{18}$) aminoalkyl, aryl, arylamino-($C_1$-$C_{18}$) alkyl, oxo, ($C_1$-$C_{18}$) aminoalkyloxy, ($C_1$-$C_{18}$) aminoalkyloxy-($C_1$-$C_{18}$) alkyl, ($C_1$-$C_{18}$) aminoalkylcarboxy, ($C_1$-$C_{18}$) aminoalkylaminocarbonyl, ($C_1$-$C_{18}$) aminoalkylcarboxamido, di($C_1$-$C_{18}$ alkyl)aminoalkyl, ($C_1$-$C_{18}$) guanidinoalkyloxy, ($C_1$-$C_{18}$) quaternary ammonium alkylcarboxy, and ($C_1$-$C_{18}$) guanidinoalkyl carboxy, provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of hydrogen, hydroxyl, an unsubstituted ($C_1$-$C_{18}$) alkyl, unsubstituted ($C_1$-$C_{18}$) hydroxyalkyl, unsubstituted ($C_1$-$C_{18}$) alkyloxy-($C_1$-$C_{18}$) alkyl, unsubstituted ($C_1$-$C_{18}$) alkylcarboxy-($C_1$-$C_{18}$) alkyl, unsubstituted ($C_1$-$C_{18}$) alkylamino-($C_1$-$C_{18}$)alkyl, unsubstituted ($C_1$-$C_{18}$) alkylamino-($C_1$-$C_{18}$) alkylamino, unsubstituted ($C_1$-$C_{18}$) alkylamino-($C_1$-$C_{18}$) alkylamino-($C_1$-$C_{18}$) alkylamino, an unsubstituted ($C_1$-$C_{18}$) aminoalkyl, an unsubstituted aryl, an unsubstituted arylamino-($C_1$-$C_{18}$) alkyl, oxo, an unsubstituted ($C_1$-$C_{18}$) aminoalkyloxy, an unsubstituted ($C_1$-$C_{18}$) aminoalkyloxy-($C_1$-$C_{18}$) alkyl, an unsubstituted ($C_1$-$C_{18}$) aminoalkylcarboxy, an unsubstituted ($C_1$-$C_{18}$) aminoalkylaminocarbonyl, an unsubstituted ($C_1$-$C_{18}$) aminoalkylcarboxamido, an unsubstituted di($C_1$-$C_{18}$ alkyl)aminoalkyl, unsubstituted ($C_1$-$C_{18}$) guanidinoalkyloxy, unsubstituted ($C_1$-$C_{18}$) quaternary ammonium alkylcarboxy, and unsubstituted ($C_1$-$C_{18}$) guanidinoalkyl carboxy.

In some embodiments, $R_3$, $R_7$, $R_{12}$, and $R_{18}$ are independently selected from the group consisting of hydrogen, an unsubstituted ($C_1$-$C_{18}$) alkyl, unsubstituted ($C_1$-$C_{18}$) hydroxyalkyl, unsubstituted ($C_1$-$C_{18}$) alkyloxy-($C_1$-$C_{18}$) alkyl, unsubstituted ($C_1$-$C_{18}$) alkylcarboxy-($C_1$-$C_{18}$) alkyl, unsubstituted ($C_1$-$C_{18}$) alkylamino-($C_1$-$C_{18}$)alkyl, unsubstituted ($C_1$-$C_{18}$) alkylamino-($C_1$-$C_{18}$) alkylamino, unsubstituted ($C_1$-$C_{18}$) alkylamino-($C_1$-$C_{18}$) alkylamino-($C_1$-$C_{18}$) alkylamino, an unsubstituted ($C_1$-$C_{18}$) aminoalkyl, an unsubstituted arylamino-($C_1$-$C_{18}$) alkyl, an unsubstituted ($C_1$-$C_{18}$) aminoalkyloxy, an unsubstituted ($C_1$-$C_{18}$) aminoalkyloxy-($C_1$-$C_{18}$) alkyl, an unsubstituted ($C_1$-$C_{18}$) aminoalkylcarboxy, an unsubstituted ($C_1$-$C_{18}$) aminoalkylaminocarbonyl, an unsubstituted ($C_1$-$C_{18}$) aminoalkylcarboxamido, an unsubstituted di($C_1$-$C_{18}$ alkyl)aminoalkyl, unsubstituted ($C_1$-$C_{18}$) guanidinoalkyloxy, unsubstituted ($C_1$-$C_{18}$) quaternary ammonium alkylcarboxy, and unsubstituted ($C_1$-$C_{18}$) guanidinoalkyl carboxy.

In some embodiments, $R_1$, $R_2$, $R_4$, $R_5$, $R_6$, $R_8$, $R_9$, $R_{10}$, $R_{11}$, $R_{13}$, $R_{14}$, $R_{15}$, $R_{16}$, and $R_{17}$ are independently selected from the group consisting of hydrogen and unsubstituted ($C_1$-$C_6$) alkyl.

In some embodiments, $R_3$, $R_7$, $R_{12}$, and $R_{18}$ are independently selected from the group consisting of hydrogen, an unsubstituted ($C_1$-$C_6$) alkyl, unsubstituted ($C_1$-$C_6$) hydroxyalkyl, unsubstituted ($C_1$-$C_{16}$) alkyloxy-($C_1$-$C_5$) alkyl, unsubstituted ($C_1$-$C_{16}$) alkylcarboxy-($C_1$-$C_5$) alkyl, unsubstituted ($C_1$-$C_{16}$) alkylamino-($C_1$-$C_5$)alkyl, ($C_1$-$C_{16}$) alkylamino-($C_1$-$C_5$) alkylamino, unsubstituted ($C_1$-$C_{16}$) alkylamino-($C_1$-$C_{16}$) alkylamino-($C_1$-$C_5$) alkylamino, an unsubstituted ($C_1$-$C_{16}$) aminoalkyl, an unsubstituted arylamino-($C_1$-$C_5$) alkyl, an unsubstituted ($C_1$-$C_5$) aminoalkyloxy, an unsubstituted ($C_1$-$C_{16}$) aminoalkyloxy-($C_1$-$C_5$) alkyl, an unsubstituted ($C_1$-$C_5$) aminoalkylcarboxy, an unsubstituted ($C_1$-$C_5$) aminoalkylaminocarbonyl, an unsubstituted ($C_1$-$C_5$) aminoalkylcarboxamido, an unsubstituted di($C_1$-$C_5$ alkyl)amino-($C_1$-$C_5$) alkyl, unsubstituted ($C_1$-$C_5$) guanidinoalkyloxy, unsubstituted ($C_1$-$C_{16}$) quaternary ammonium alkylcarboxy, and unsubstituted ($C_1$-$C_{16}$) guanidinoalkylcarboxy.

In some embodiments, $R_1$, $R_2$, $R_4$, $R_5$, $R_6$, $R_8$, $R_{10}$, $R_{11}$, $R_{14}$, $R_{16}$, and $R_{17}$ are each hydrogen; and $R_9$ and $R_{13}$ are each methyl.

In some embodiments, $R_3$, $R_7$, $R_{12}$, and $R_{18}$ are independently selected from the group consisting of aminoalkyloxy; aminoalkylcarboxy; alkylaminoalkyl; alkoxycarbonylalkyl; alkylcarbonylalkyl; di(alkyl)aminoalkyl; alkylcarboxyalkyl; and hydroxyalkyl.

In some embodiments, $R_3$, $R_7$, and $R_{12}$ are independently selected from the group consisting of aminoalkyloxy and aminoalkylcarboxy; and $R_{18}$ is selected from the group consisting of alkylaminoalkyl; alkoxycarbonylalkyl; alkylcarbonyloxyalkyl; di(alkyl)aminoalkyl; alkylaminoalkyl; alkyoxycarbonylalkyl; alkylcarboxyalkyl; and hydroxyalkyl.

In some embodiments, $R_3$, $R_7$, and $R_{12}$ are the same. In some embodiments, $R_3$, $R_7$, and $R_{12}$ are aminoalkyloxy. In some embodiments, $R_{18}$ is alkylaminoalkyl. In some embodiments, $R_{18}$ is alkoxycarbonylalkyl. In some embodiments, $R_{18}$ is di(alkyl)aminoalkyl. In some embodiments, $R_{18}$ is alkylcarboxyalkyl. In some embodiments, $R_{18}$ is hydroxyalkyl. In some embodiments, $R_3$, $R_7$, and $R_{12}$ are aminoalkylcarboxy.

In some embodiments, $R_3$, $R_7$, $R_{12}$, and $R_{18}$ are independently selected from the group consisting of aminoalkyloxy; aminoalkylcarboxy; alkylaminoalkyl; di-(alkyl)aminoalkyl; alkoxycarbonylalkyl; and alkylcarboxyalkyl.

In some embodiments, $R_3$, $R_7$, and $R_{12}$ are independently selected from the group consisting of aminoalkyloxy and aminoalkylcarboxy, and wherein $R_{18}$ is selected from the group consisting of alkylaminoalkyl; di-(alkyl)aminoalkyl; alkoxycarbonylalkyl; and alkylcarboxyalkyl.

In some embodiments, $R_3$, $R_7$, and $R_{12}$ are independently selected from the group consisting of aminoalkyloxy and aminoalkylcarboxy, and wherein $R_{18}$ is selected from the group consisting of alkylaminoalkyl; di-(alkyl)aminoalkyl; and alkoxycarbonylalkyl.

In some embodiments, R3, R7, R12, and R18 are independently selected from the group consisting of amino-$C_3$-alkyloxy; amino-$C_3$-alkyl-carboxy; $C_8$-alkylamino-$C_5$-alkyl; $C_{12}$-alkylamino-$C_5$-alkyl; $C_{13}$-alkylamino-$C_5$-alkyl; $C_{16}$-alkylamino-$C_5$-alkyl; di-($C_5$-alkyl)amino-$C_5$-alkyl; $C_6$-alkoxy-carbonyl-$C_4$-alkyl; $C_8$-alkoxy-carbonyl-$C_4$-alkyl; $C_{10}$-alkoxy-carbonyl-$C_4$-alkyl; $C_6$-alkyl-carboxy-$C_4$-alkyl; $C_8$-alkyl-carboxy-$C_4$-alkyl; and $C_{10}$-alkyl-carboxy-$C_4$-alkyl.

In some embodiments, $R_3$, $R_7$, $R_{12}$, and $R_{18}$ are independently selected from the group consisting of amino-$C_3$-alkyloxy; amino-$C_3$-alkyl-carboxy; $C_8$-alkylamino-$C_5$-alkyl; $C_{12}$-alkylamino-$C_5$-alkyl; $C_{13}$-alkylamino-$C_5$-alkyl; $C_{16}$-alkylamino-$C_5$-alkyl; di-($C_5$-alkyl)amino-$C_5$-alkyl; $C_6$-alkoxy-carbonyl-$C_4$-alkyl; $C_8$-alkoxy-carbonyl-$C_4$-alkyl; and $C_{10}$-alkoxy-carbonyl-$C_4$-alkyl.

In some embodiments, $R_3$, $R_7$, and $R_{12}$, are independently selected from the group consisting of amino-$C_3$-alkyloxy or amino-$C_3$-alkyl-carboxy, and wherein $R_{18}$ is selected from the group consisting of $C_8$-alkylamino-$C_5$-alkyl; $C_{12}$-alkylamino-$C_5$-alkyl; $C_{13}$-alkylamino-$C_5$-alkyl; $C_{16}$-alkylamino-$C_5$-alkyl; di-($C_5$-alkyl)amino-$C_5$-alkyl; $C_6$-alkoxy-carbonyl-$C_4$-alkyl; $C_8$-alkoxy-carbonyl-$C_4$-alkyl; $C_{10}$-alkoxy-carbonyl-$C_4$-alkyl; $C_6$-alkyl-carboxy-$C_4$-alkyl; $C_8$-alkyl-carboxy-$C_4$-alkyl; and $C_{10}$-alkyl-carboxy-$C_4$-alkyl.

In some embodiments, $R_3$, $R_7$, and $R_{12}$, are independently selected from the group consisting of amino-$C_3$-alkyloxy or amino-$C_3$-alkyl-carboxy, and wherein $R_{18}$ is selected from the group consisting of $C_8$-alkylamino-$C_5$-alkyl; $C_{12}$-alkylamino-$C_5$-alkyl; $C_{13}$-alkylamino-$C_5$-alkyl; $C_{16}$-alkylamino-$C_5$-alkyl; di-($C_5$-alkyl)amino-$C_5$-alkyl; $C_6$-alkoxy-carbonyl-$C_4$-alkyl; $C_8$-alkoxy-carbonyl-$C_4$-alkyl; and $C_{10}$-alkoxy-carbonyl-$C_4$-alkyl.

In some embodiments, $R_3$, $R_7$, $R_{12}$, and $R_{18}$ are independently selected from the group consisting of amino-$C_3$-alkyloxy; amino-$C_3$-alkyl-carboxy; amino-$C_2$-alkylcarboxy; $C_8$-alkylamino-$C_5$-alkyl; $C_8$-alkoxy-carbonyl-$C_4$-alkyl; $C_{10}$-alkoxy-carbonyl-$C_4$-alkyl; $C_8$-alkyl-carbonyl-$C_4$-alkyl; di-($C_5$-alkyl)amino-$C_5$-alkyl; $C_{13}$-alkylamino-$C_5$-alkyl; $C_6$-alkoxy-carbonyl-$C_4$-alkyl; $C_6$-alkyl-carboxy-$C_4$-alkyl; $C_{16}$-alkylamino-$C_5$-alkyl; $C_{12}$-alkylamino-$C_5$-alkyl; and hydroxy($C_5$)alkyl.

In some embodiments, $R_{18}$ is selected from the group consisting of $C_8$-alkylamino-$C_5$-alkyl or $C_8$-alkoxy-carbonyl-$C_4$-alkyl.

In some embodiments, at least $R_{18}$ can have the following structure:

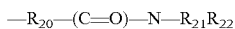

wherein $R_{20}$ is omitted or alkyl, alkenyl, alkynyl, or aryl, and $R_{21}$ and $R_{22}$ are independently selected from the group consisting of hydrogen, alkyl, alkenyl, alkynyl, or aryl, provided that at least one of $R_{21}$ and $R_{22}$ is not hydrogen.

In some embodiments, $R_{21}$ and $R_{22}$ are independently selected from the group consisting of hydrogen, $C_1$-$C_{24}$ alkyl, $C_2$-$C_{24}$ alkenyl, $C_2$-$C_{24}$ alkynyl, $C_6$ or $C_{10}$ aryl, 5 to 10 membered heteroaryl, 5 to 10 membered heterocyclyl, $C_{7-13}$ aralkyl, (5 to 10 membered heteroaryl)-$C_1$-$C_6$ alkyl, $C_{3-10}$ carbocyclyl, $C_{4-10}$ (carbocyclyl)alkyl, (5 to 10 membered heterocyclyl)-$C_1$-$C_6$ alkyl, amido, and a suitable amine protecting group, provided that at least one of $R_{21}$ and $R_{22}$ is not hydrogen. In some embodiments, $R_{21}$ and $R_{22}$, together with the atoms to which they are attached, form a 5 to 10 membered heterocyclyl ring.

In some embodiments, one or more of rings A, B, C, and D is heterocyclic. In some embodiments, rings A, B, C, and D are non-heterocyclic.

In some embodiments, the CSA compound is a compound of Formula IV, which is a subset of Formula III, or salt thereof, having a steroidal backbone:

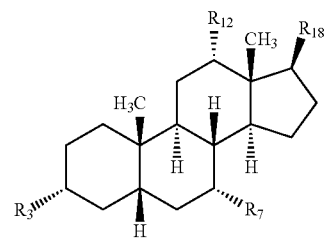

(IV)

In some embodiments, $R_3$, $R_7$, and $R_{12}$ are independently selected from the group consisting of hydrogen, an unsubstituted ($C_1$-$C_{22}$) alkyl, unsubstituted ($C_1$-$C_{22}$) hydroxyalkyl, unsubstituted ($C_1$-$C_{22}$) alkyloxy-($C_1$-$C_{22}$) alkyl, unsubstituted ($C_1$-$C_{22}$) alkylcarboxy-($C_1$-$C_{22}$) alkyl, unsubstituted ($C_1$-$C_{22}$) alkylamino-($C_1$-$C_{22}$)alkyl, unsubstituted ($C_1$-$C_{22}$) alkylamino-($C_1$-$C_{22}$) alkylamino, unsubstituted ($C_1$-$C_{22}$) alkylamino-($C_1$-$C_{22}$) alkylamino-($C_1$-$C_{18}$) alkylamino, an unsubstituted ($C_1$-$C_{22}$) aminoalkyl, an unsubstituted arylamino-($C_1$-$C_{22}$) alkyl, an unsubstituted ($C_1$-$C_{22}$) aminoalkyloxy, an unsubstituted ($C_1$-$C_{22}$) aminoalkyloxy-($C_1$-$C_{22}$) alkyl, an unsubstituted ($C_1$-$C_{22}$) aminoalkylcarboxy, an unsubstituted ($C_1$-$C_{22}$) aminoalkyl-aminocarbonyl, an unsubstituted ($C_1$-$C_{22}$) aminoalkylcarboxamido, an unsubstituted di($C_1$-$C_{22}$ alkyl)aminoalkyl, unsubstituted ($C_1$-$C_{22}$) guanidinoalkyloxy, unsubstituted ($C_1$-$C_{22}$) quaternary ammonium alkylcarboxy, and unsubstituted ($C_1$-$C_{22}$) guanidinoalkyl carboxy.

In some embodiments, $R_3$, $R_7$, and $R_{12}$ are independently selected from the group consisting of hydrogen, an unsubstituted ($C_1$-$C_6$) alkyl, unsubstituted ($C_1$-$C_6$) hydroxyalkyl, unsubstituted ($C_1$-$C_{16}$) alkyloxy-($C_1$-$C_5$) alkyl, unsubstituted ($C_1$-$C_{16}$) alkylcarboxy-($C_1$-$C_5$) alkyl, unsubstituted ($C_1$-$C_{16}$) alkylamino-($C_1$-$C_5$)alkyl, unsubstituted ($C_1$-$C_{16}$) alkylamino-($C_1$-$C_5$) alkylamino, unsubstituted ($C_1$-$C_{16}$) alkylamino-($C_1$-$C_{16}$) alkylamino-($C_1$-$C_5$) alkylamino, an unsubstituted ($C_1$-$C_{16}$) aminoalkyl, an unsubstituted arylamino-($C_1$-$C_5$) alkyl, an unsubstituted ($C_1$-$C_5$) aminoalkyloxy, an unsubstituted ($C_1$-$C_{16}$) aminoalkyloxy-($C_1$-$C_5$) alkyl, an unsubstituted ($C_1$-$C_5$) aminoalkylcarboxy, an unsubstituted ($C_1$-$C_5$) aminoalkylaminocarbonyl, an unsubstituted ($C_1$-$C_5$) aminoalkylcarboxamido, an unsubstituted di($C_1$-$C_5$ alkyl)amino-($C_1$-$C_5$) alkyl, unsubstituted ($C_1$-$C_5$) guanidinoalkyloxy, unsubstituted ($C_1$-$C_{16}$) quaternary ammonium alkylcarboxy, and unsubstituted ($C_1$-$C_{16}$) guanidinoalkylcarboxy.

In some embodiments, $R_3$, $R_7$, and $R_{12}$ are independently selected from the group consisting of aminoalkyloxy; aminoalkylcarboxy; alkylaminoalkyl; alkoxycarbonylalkyl; alkylcarbonylalkyl; di(alkyl)aminoalkyl; alkylcarboxyalkyl; and hydroxyalkyl.

In some embodiments, $R_3$, $R_7$, and $R_{12}$ are independently selected from the group consisting of aminoalkyloxy and aminoalkylcarboxy.

In some embodiments, $R_3$, $R_7$, and $R_{12}$ are the same. In some embodiments, $R_3$, $R_7$, and $R_{12}$ are aminoalkyloxy. In some embodiments, $R_3$, $R_7$, and $R_{12}$ are aminoalkylcarboxy.

In some embodiments, $R_3$, $R_7$, and $R_{12}$ are independently selected from the group consisting of amino-$C_3$-alkyloxy; amino-$C_3$-alkyl-carboxy; $C_8$-alkylamino-$C_5$-alkyl; $C_8$-alkoxy-carbonyl-$C_4$-alkyl; $C_8$-alkyl-carbonyl-$C_4$-alkyl; di-($C_5$-alkyl)amino-$C_5$-alkyl; $C_{13}$-alkylamino-$C_5$-alkyl; $C_6$-alkoxy-carbonyl-$C_4$-alkyl; $C_6$-alkyl-carboxy-$C_4$-alkyl; and $C_{16}$-alkylamino-$C_5$-alkyl.

In some embodiments, CSA compounds as disclosed herein can be a compound of Formula I, Formula II, Formula III, Formula IV, or salts thereof wherein at least $R_{18}$ of the steroidal backbone includes amide functionality in which the carbonyl group of the amide is positioned between the amido nitrogen of the amide and fused ring D of the steroidal backbone. For example, any of the embodiments described above can substitute $R_{18}$ for an $R_{18}$ including amide functionality in which the carbonyl group of the amide is positioned between the amido nitrogen of the amide and fused ring D of the steroidal backbone.

In some embodiments, one or more of $R_3$, $R_7$, or $R_{12}$ may include a guanidine group as a cationic functional group and may be bonded to the steroid backbone by an ether linkage. For example, one or more of $R_3$, $R_7$, or $R_{12}$ may be a guanidinoalkyloxy group. An example includes $H_2N$—C(=NH)—NH-alkyl-O—,

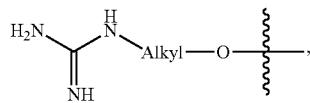

wherein the alkyl portion is defined as with the embodiments described above. In a preferred embodiment, the alkyl portion is a straight chain with 3 carbon atoms, and therefore one or more of $R_3$, $R_7$, or $R_{12}$ may be a guanidinopropyloxy group.

One of skill in the art will recognize that other cationic functional groups may be utilized, and that the cationic functional groups may be bonded to the steroid backbone through a variety of other tethers or linkages. For example, the cationic functional groups may be bonded to the steroid backbone by an ester linkage. For example, one or more of $R_3$, $R_7$, or $R_{12}$ may be an aminoalkylcarboxy or guanidinoalkylcarboxy, such as $H_2N$-alkyl-C(=O)—O— or $H_2N$—C(=NH)—NH-alkyl-C(=O)—O—, wherein the alkyl portion is defined as with the embodiments described above. In other embodiments, the cationic functional groups may be bonded to the steroid backbone by an amide linkage. For example, one or more of $R_3$, $R_7$, or $R_{12}$ may be an aminoalkylcarbonylamino (i.e. aminoalkylcarboxamido) or guanidinoalkylcarbonylamino (i.e. guanidinoalkylcarboxamido), such as $H_2N$-alkyl-C(=O)—NH— or $H_2N$—C(=NH)—NH-alkyl-C(=O)—NH—, wherein the alkyl portion is defined as with the embodiments described above.

Additionally, one of skill in the art will recognize that the tethers may be of varying lengths. For example, the length between the steroid backbone and the cationic functional group (e.g., amino or guanidino group), may be between 1 and 15 atoms or even more than 15 atoms. In other embodiments, the length may be between 1 and 8 atoms. In a preferred embodiment, the length of the tether is between two and four atoms. In other embodiments, there is no tether, such that the cationic functional group is bonded directly to the steroid backbone.

One of skill in the art will also note that the various cationic functional groups of the present disclosure may be utilized in combination, such that one or more of $R_3$, $R_7$, or $R_{12}$ may include one variation of cationic functional group while one or more of another of $R_3$, $R_7$, or $R_{12}$ of the same compound may include a different variation of cationic functional group. Alternatively, two or more of $R_3$, $R_7$, or $R_{12}$ may include the same cationic functional group, or all of $R_3$, $R_7$, or $R_{12}$ may include the same cationic functional group (in embodiments where all of $R_3$, $R_7$, or $R_{12}$ are cationic functional groups).

Additionally, although in one or more cationic functional groups are disposed at $R_3$, $R_7$, or $R_{12}$, one of skill in the art will recognize that in other embodiments, $R_3$, $R_7$, or $R_{12}$ may not be cationic functional groups and/or one or more cationic functional groups may be disposed at other locations of the steroid backbone. For example, one or more cationic functional groups may be disposed at $R_1$, $R_2$, $R_3$, $R_4$, $R_6$, $R_7$, $R_{11}$, $R_{12}$, $R_{15}$, $R_{16}$, $R_{17}$, and/or $R_{18}$.

The compounds and compositions disclosed herein are optionally prepared as salts. The term "salt" as used herein is a broad term, and is to be given its ordinary and customary meaning to a skilled artisan (and is not to be limited to a special or customized meaning), and refers without limitation to a salt of a compound. In some embodiments, the salt is an acid addition salt of the compound. Salts can be obtained by reacting a compound with inorganic acids such as hydrohalic acid (e.g., hydrochloric acid or hydrobromic acid), sulfuric acid, nitric acid, and phosphoric acid. Salts can also be obtained by reacting a compound with an organic acid such as aliphatic or aromatic carboxylic or sulfonic acids, for example formic acid, acetic acid, propionic acid, glycolic acid, pyruvic acid, malonic acid, maleic acid, fumaric acid, trifluoroacetic acid, benzoic acid, cinnamic acid, mandelic acid, succinic acid, lactic acid, malic acid, tartaric acid, citric acid, ascorbic acid, nicotinic acid, methanesulfonic acid, ethanesulfonic acid, p-toluensulfonic acid, salicylic acid, stearic acid, muconic acid, butyric acid, phenylacetic acid, phenylbutyric acid, valproic acid, 1,2-ethanedisulfonic acid, 2-hydroxyethanesulfonic acid, benzenesulfonic acid, 2-naphthalenesulfonic acid, or naphthalenesulfonic acid. Salts can also be obtained by reacting a compound with a base to form a salt such as an ammonium salt, an alkali metal salt, such as a lithium, sodium or a potassium salt, an alkaline earth metal salt, such as a calcium, magnesium or aluminum salt, a salt of organic bases such as dicyclohexylamine, N-methyl-D-glucamine, tris(hydroxymethyl)methylamine, $C_1$-$C_7$ alkylamine, cyclohexylamine, dicyclohexylamine, triethanolamine, ethylenediamine, ethanolamine, diethanolamine, triethanolamine, tromethamine, and salts with amino acids such as arginine and lysine; or a salt of an inorganic base, such as aluminum hydroxide, calcium hydroxide, potassium hydroxide, sodium carbonate, sodium hydroxide, or the like.

In some embodiments, the salt is a hydrochloride salt. In some embodiments, the salt is a mono-hydrochloride salt, a di-hydrochloride salt, a tri-hydrochloride salt, or a tetra-hydrochloride salt. Additional examples of salts include sulfuric acid addition salts, sulfonic acid addition salts, disulfonic acid addition salts, 1,5-naphthalenedisulfonic acid addition salts, sulfate salts, and bisulfate salts.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

VI. Examples

An Appendix is attached hereto describing various examples illustrating the effectiveness of treatment compositions as described herein in killing microbes, including biofilms, without damaging ciliated cells.

Example 1

To observe the impact of pluronic micelles on ceragenins activity and to optimize ceragenin formulation for use in treating biofilm-based infections in the lung, the impact of a lead ceragenin, CSA-131, was studied, with and without pluronic, on cilia beating and the inhibition of bacterial and fungal growth in vitro and in tracheal and lung tissue explants. It was found that the use of pluronic with relatively high concentrations of CSA-131 leaves cilia beating intact, and the pluronic has no impact on the antimicrobial activities of CSA-131. These results suggest that the formulation of ceragenin CSA-131 in pluronic micelles allow use of high concentrations of this antimicrobial, sufficient to eliminate biofilms without negatively impacting cilia function.

Microbial Cultures

*Staphylococcus aureus* (ATCC 25923) and *Pseudomonas aeruginosa* (ATCC 47085 (PA01)) were grown from fresh colonies in trypticase soy broth (TSB) and incubated overnight at 37° C. Fungal cultures, *Candida albicans* (ATCC 90028) and *Candida auris* (CDC 0382, 0384, 0387, and 0389), were grown overnight in sabouraud dextrose broth (SDB) or Roswell Park Memorial Institute medium (RPMI). Cultures of bacteria and fungi were centrifuged, and pellets were washed three times with phosphate buffered saline (PBS) and further resuspended in fresh PBS. Bacterial cultures were diluted in TSB and fungal cultures were diluted in SDB or RPMI to 103 or 106 CFU/mL (optical density (OD) readings at 600 nm).

Susceptibility Testing in the Presence or Absence of Pluronic Minimum Inhibitory Concentration (MIC)

Minimum inhibitory concentrations (MICs) were measured using the broth microdilution protocol described by the Clinical and Laboratory Standards Institute [26, 27]. Briefly, two-fold dilutions of CSA-131 were dispensed in separate wells of a 96-well plate. Aliquots (100 µL) of a prepared inoculum (106 CFU/mL for bacteria and 103 CFU/mL for fungi) were added, and plates were incubated at 37° C. for 18-20 h. Bacterial or fungal growth was visually observed to determine the MICs. Negative and positive controls were included for each set of MIC measurements. For studies with pluronic, the surfactant was added at 4% and 5% to the initial inocula in each experiment. Measurements were performed in triplicate for all susceptibility tests.

Determination of Antifungal and Antibacterial Susceptibilities of Biofilms by XTT Assay Biofilm formation by selected bacterial and fungal strains was quantified by measuring metabolic activity within biofilms using 2,3-bis-(2-methoxy-4-nitro-5-sulfophenyl)-2H-tetrazolium-5-carboxanilide (XTT). Biofilms were formed in 96-well plates and incubated for 48 h at 37° C. After three washes with PBS to remove planktonic cells, CSA-131 (100 µg/mL) in the presence or absence of 4% or 5% pluronic was added to the wells and incubated for 24 h. After incubation, the wells were carefully washed with PBS. A solution of 10 mM menadione in 100% acetone was added to an XTT solution (0.5 mg/mL) and mixed. An aliquot of the XTT/menadione solution (100 µL) was added to each well. Each plate was then wrapped in aluminum foil and incubated for 2-3 h at 37° C. To prepare to read the optical density, aliquots of the supernatant (70 µL) were removed from each well. Using a microtiter plate reader, colorimetric changes were measured at 490 nm. The percent of biofilm survival for each well containing CSA-131 with or without pluronic was calculated in comparison to the biofilm formed in the absence of the ceragenin (control).

Determination of Minimum Biofilm Eradication Concentrations (MBEC)

Inocula (106 CFU/mL) of bacterial and fungal strains (*P. aeruginosa, S. aureus, C. albicans*, and *C. auris*) were incubated at 37° C. for 48 h in 1 mL of TSB or SDB in 96-well plates. Following incubation, the growth medium was gently removed, and wells were washed three times with sterile PBS. CSA-131 (100 µg/mL), in TSB or SDB and in the presence or absence of pluronic (4% or 5%), was added to the wells at concentrations ranging from 1 to 256 µg/mL, and each plate was incubated at 37° C. for 24 h. Wells, including well edges, were scraped thoroughly with a plastic spatula. Well contents were removed in 1 mL of neutralizing broth (Dey-Engley, Sigma-Aldrich) and placed in a sonicating water bath (Fisher Scientific FS60, 42 kHz, 100 W, Pittsburgh, PA, USA) to disrupt biofilms. After 15 min, the resulting samples were serially diluted, and bacterial samples were plated on TSA while fungal samples were plated on SDA. After 24 h or 48 h of incubation at 37° C., colonies were counted and MBECs were determined. The minimum biofilm eradication concentration (MBEC) was defined as the lowest concentration of antibiotic that prevented bacterial regrowth.

The impact of pluronic, at 4% and 5% of the growth medium, on the antibacterial and antifungal activity of ceragenin CSA-131 was initially determined. The amphiphilic nature of the ceragenin makes it likely that it associates well with pluronic micelles. At issue is whether the ceragenin can effectively escape micelles to exert antimicrobial effects. Earlier reports with bacteria [23, 24] demonstrated that pluronic did not substantially affect antibacterial activity. The MICs and MBECs of CSA-131 alone and in the presence of pluronic at 4% and 5% are given in Table 1 below. MBECs are the concentrations required to eliminate biofilms, including persister cells, to detection limits. With both *S. aureus* and *P. aeruginosa*, MICs were unchanged in the presence of pluronic, as observed previously. Notably, *Candida* spp. MICS were also unaffected by pluronic, even though these are eukaryotic organisms. Notably, MBECs with both bacteria and fungi were unchanged in the presence of pluronic

TABLE 1

Minimum inhibitory concentration (MIC) and minimum biofilm eradication concentration (MBEC) of CSA-131 with bacteria and fungi in the absence or presence of pluronic.

| Strains | MIC (MBEC) (µg/mL) | | |
| --- | --- | --- | --- |
| | CSA-131 | CSA-131 + 4% Pluronic | CSA-131 + 5% Pluronic |
| S. aureus ATCC 25923 | 1 (100) | 1 (100) | 1 (100) |
| P. aeruginosa ATCC 47085 | 2 (100) | 2 (100) | 2 (100) |
| C. auris CDC 382 | 0.5 (82) | 0.5 (82) | 0.5 (82) |
| C. auris CDC 384 | 0.5 (48) | 0.5 (48) | 0.5 (48) |
| C. auris CDC 387 | 0.5 (64) | 0.5 (64) | 0.5 (48) |
| C. auris CDC 389 | 0.5 (48) | 0.5 (48) | 0.5 (48) |
| C. albicans ATCC 90028 | 0.5 (48) | 0.5 (48) | 0.5 (48) |

Results from studies given in Table 1 suggest that a concentration of ceragenin of 100 µg/mL is sufficient to eradicate established bacterial and fungal biofilms. Consequently, this concentration was used as a target for antibacterial and antifungal activity, as well as in tolerability studies with trachea and lung explants. A key preliminary question in these studies is whether the pluronic alone has any effect on bacteria and fungi. To answer this question, the target concentration of CSA-131 (100 µg/mL) was prepared with and without pluronic, and antibiofilm activity was measured. In these assays, biofilms were generated over 48 h, and after treatment, bacterial and fungal counts were determined by plating organisms freed from biofilms and counting colonies. Detection limits for the experiments were two logs. At 100 µg/mL, with and without pluronic, CSA-131 lowered bacterial and fungal counts to the detection limit (>four-log reduction (99.99% reduction)). Pluronic alone did not significantly influence microbial counts from the biofilms.

Figure 2:
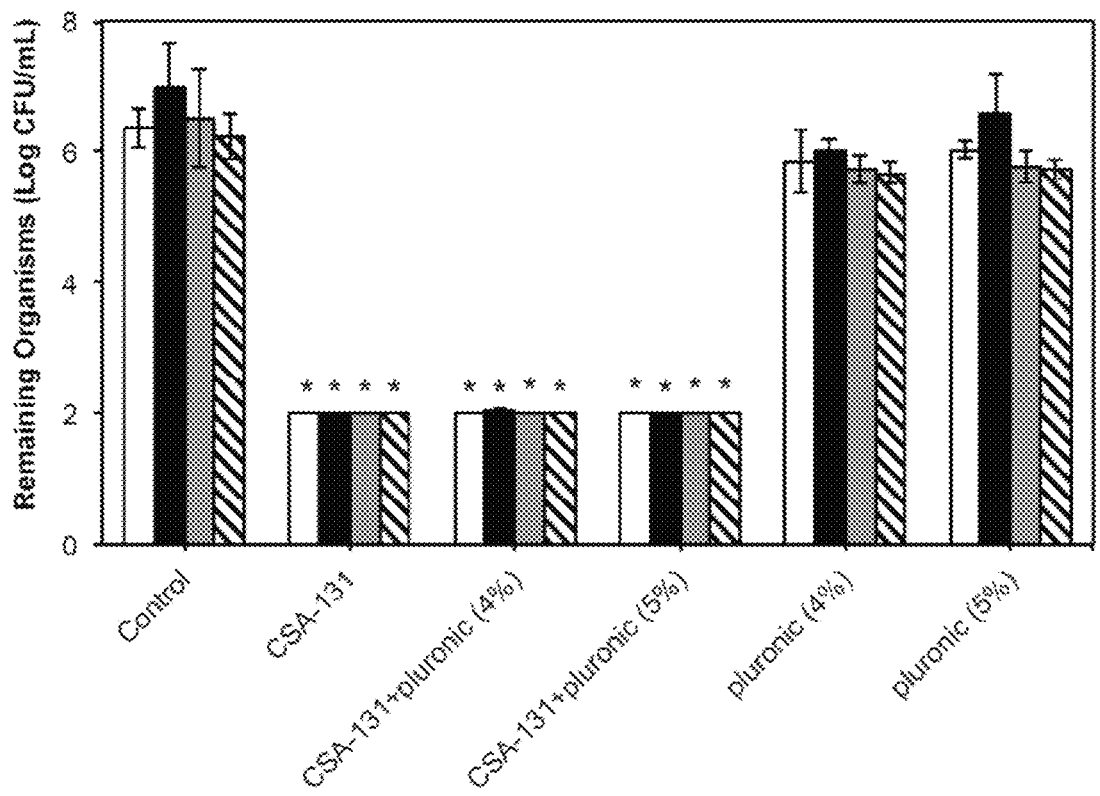
FIG. 2 is a bar graph comparing the antimicrobial effects of CSA compositions with and without micelles on various bacteria and fungi, and against a control without any CSA and pluronic without any CSA.

FIG. 2 is a bar graph that graphically illustrates the antimicrobial effect of CSA-131, with and without Pluronic, and also compared to a control and pluronic by itself, without any CSA-131. Antibiofilm results were determined through the plating of microorganisms freed from biofilms, culturing, and plate counting. In FIG. 2, white bars show remaining S. aureus (ATCC 25923); black bars show remaining P. aeruginosa (ATCC 47085); gray bars show remaining C. albicans (ATCC 90028); hashed bars show remaining C. auris (CDC 384). The Detection limit was 2 logs. * indicates p<0.05 relative to controls and to pluronic alone.

To corroborate the antibiofilm data from counting bacterial and fungal colonies, a colorimetric assay was performed to quantify biofilms remaining on surfaces after treatment. Results were normalized to untreated controls.

Figure 3:
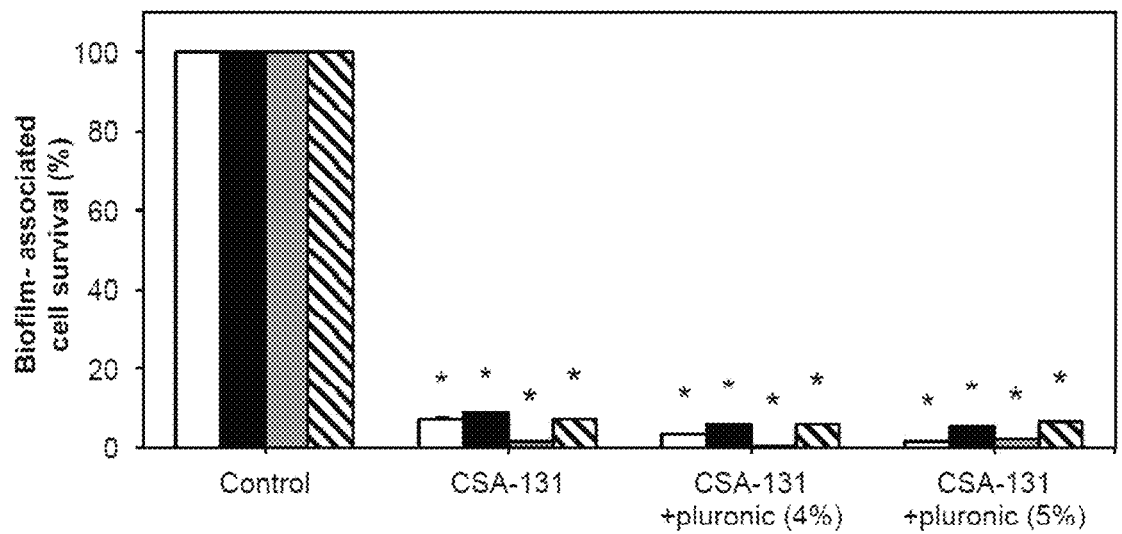
FIG. 3 is a bar graph comparing the antibiofilm effects of CSA compositions with and without micelles on various bacteria and fungi, and against a control without any CSA.

FIG. 3 is a bar graph that graphically illustrates the antimicrobial effect of CSA-131, with and without Pluronic, and also compared to a control. Significant decreases in biofilm were observed, but differences between CSA-131 alone and with pluronic were not significant. Antibiofilm results determined through colorimetric (XTT) assay represented as percent survival. In FIG. 3, white bars show biofilm associated survival of S. aureus (ATCC 25923); black bars show biofilm associated survival of P. aeruginosa (ATCC 47085); gray bars show biofilm associated survival of C. albicans (ATCC 90028); hashed bars show biofilm associated survival of C. auris (CDC 384). * indicates p<0.05 relative to controls.

Measurement of Kinetics of Bactericidal and Fungicidal Activity

Cultures of S. aureus, P. aeruginosa, and C. albicans were prepared as described for MIC measurements and placed in 96-well plates (106 CFU for bacteria and 103 CFU for fungi) with or without CSA-131 (100 µg/mL), with or without pluronic (4%), in TSB (with bacteria) or SDB (with fungi). Cultures were incubated at 37° C. At 5, 15, 30, 60, and 120 min, aliquots were removed from each well and added to neutralizing buffer to ensure that no further antibacterial activity occurred. These samples were then serially diluted and plated on TSA or SDA. Cultures were incubated at 37° C. for 24 h or 48 h, and colonies were counted and recorded.

A possible consequence of the association of CSA-131 with pluronic micelles would be the slowing of the kinetic antimicrobial activities of this ceragenin relative to the ceragenin alone. Bacterial and fungal counts were measured over time with CSA-131 (100 µg/mL) and CSA-131 with pluronic (4%). Results from an experiment with P. aeruginosa (ATCC 47085) are shown in FIG. 4.

Figure 4:
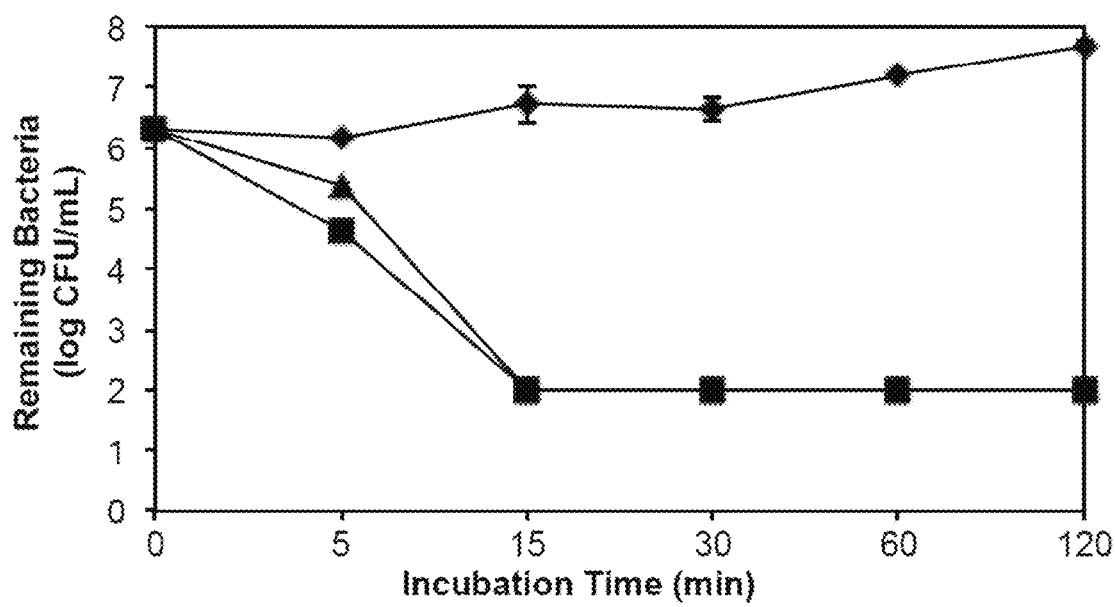
FIG. 4 is a line graph comparing the kinetic antibacterial activity of CSA compositions with micelles compared to a control without CSA.
Figure 5A:
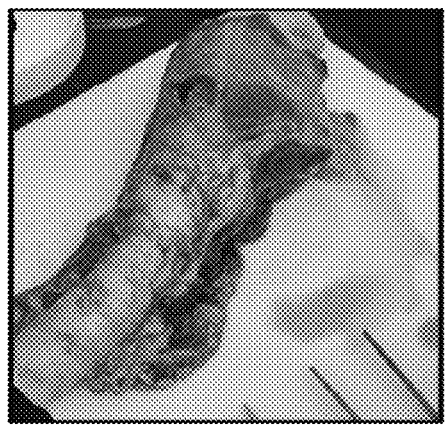
FIGS. 5A-5E illustrate example steps used in harvesting and testing porcine trachea explants with respect to cilia function.
Figure 5B:
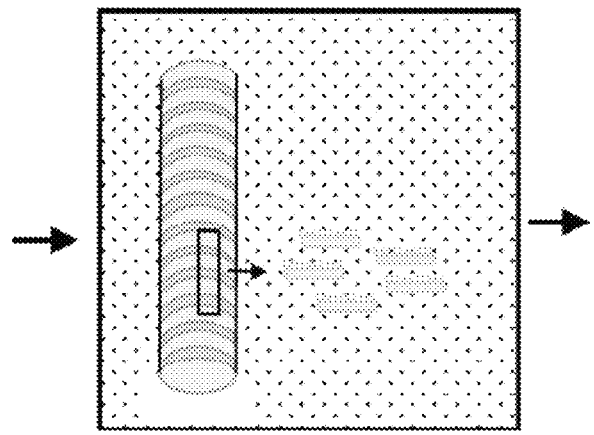
Figure 5C:
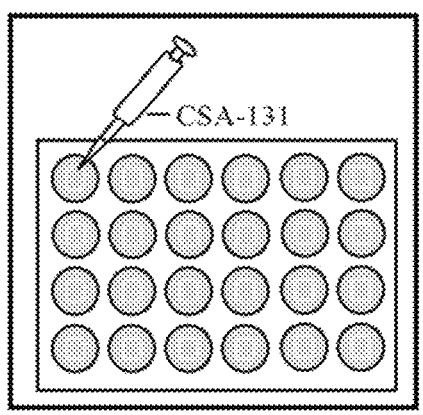
Figure 5D:
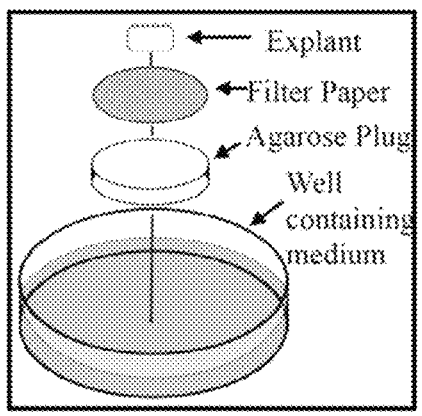
Figure 5E:
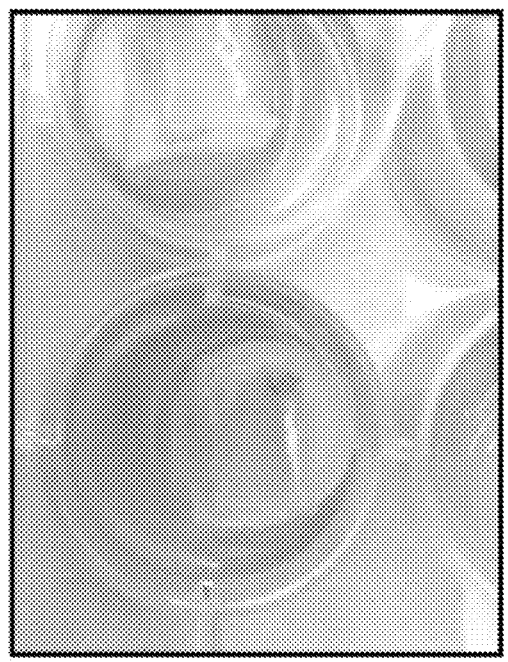

FIG. 4 is a line graph comparing the kinetic antibacterial activity of CSA compositions with micelles compared to a control without CSA. Inocula of just over 106 CFU/mL were reduced to the detection limit within 15 min. At 5 min, there was a small difference in bacterial counts with CSA-131 alone and CSA-131 with pluronic. With S. aureus and with C. albicans, no significant differences between kinetic activity of the ceragenin alone and with pluronic were observed (data not shown). In FIG. 4, kinetic antibacterial activity against P. aeruginosa of CSA-131 (100 µg/mL) is shown by black squares), CSA-131 (100 µg/mL) with pluronic (4%) (black triangles); the untreated control is shown by black diamonds. Detection limit was two logs.

Example 2

In this example, the effect of CSA compositions with and without micelles was tested using ciliated porcine lung tissue. Having established the antibiofilm activity of CSA-131 in the presence of pluronic, the impact of formulations of CSA-131 on ciliated tissue explants from porcine tracheas was determined. The cilia on these tissues play a critical role in removing particulate matter from the lung and trachea; consequently, it was important to establish that CSA-131 can exert antibacterial and antifungal activity without damaging cilia. Furthermore, the presence of undamaged cilia is an indication that the underlying epithelial and goblet cells are unaffected by ceragenin treatment. An ex vivo assay was used to evaluate pluronic-containing formulations, and in this assay the beating of cilia can be actively observed. These observations were used to determine the concentration of pluronic, with CSA-131 (100 µg/mL), that would not impact cilia function, and by extension leave undamaged the underlying epithelial and goblet cells. This method involves sectioning porcine trachea, supported in a nutrient medium, placing small beads on one side of the explant, and measuring the transfer (clearance) of the beads to the other side of the explants (FIG. 5). In our hands, we could reproducibly measure bead clearance one hour after sectioning and treatment. Twelve explants were used for each test condition, and the results are reported as the number clearing beads in a given amount of time.

Preparation of Tracheal Explants

Normal healthy porcine trachea and lung tissue was excised very fresh from slaughter. After aseptic collection, whole tissues were transported in a 1:1 mixture of Dulbecco's modified Eagle's medium (DMEM) and RPMI, which was pre-warmed and supplemented with penicillin-streptomycin-glutamine 100× (Hyclone, Logan, UT, USA). Explants were washed by tissue immersion three to four times in warm, fresh DMEM/RPMI media. Explants were maintained by continuous immersion in DMEM/RPMI media in a 5% CO2-95% air mixture in a humidified incubator at 37° C. Ethics statement: Trachea and lung materials were obtained from a local butcher (Circle V Meat Co., Spanish Fork, UT, USA) and were sourced from animals slaughtered for human consumption; hence, ethical approval was not required for this research.

Latex Bead Clearance Assay

FIGS. 5A-5E illustrate example steps used in harvesting and testing porcine trachea explants with respect to cilia function. Tracheas were washed and extra exterior tissues to the cartilage were removed. Tracheas were opened and cut into approximately 2×1 cm explants consisting of the respiratory mucosa and underlying cartilage. Explants were then immersed in different concentrations of CSA-131, with and without pluronic, in the DMEM/RPMI mixture in 24-well plates for 1 h in a humidified incubator at 37° C. with 5% $CO_2$. Explants were then placed on small circular filter papers, which were placed on top of 1% agarose gel plugs bathed in medium in 6-well plates. To determine cilia activity on explants, epithelial surfaces were tested via a bead clearance assay 1 h post treatment with CSA-131 (100 μg/mL), with or without pluronic (1%, 2%, 3%, 4%, and 5%). Five microliters of a suspension of 1 μm diameter polystyrene microsphere beads (Polysciences, Inc., Warrington, PA, USA) were pipetted on one edge of epithelial surfaces and evaluated for their complete clearance (movement) across the surface with categorization of clearance in under 10 min, between 10 and 20 min, between 20 and 30 min, and no clearance (>30 min). Independent replicates were completed for each time point. Outcomes were then counted and a percentage of clearance was determined.

With no treatment with CSA-131, all 12 explants cleared the applied beads within 20 min, and 10 of the explants cleared the beads in less than 10 min. Treatment of the explants with CSA-131 at 100 μg/mL for one hour caused a majority (six of 12) to lose the ability to clear the beads. Increasing amounts of pluronic (from 1 to 5%) restored the ability of the cilia to clear the beads, and at 5% pluronic, bead clearance was the same as the control. Table 2 shows the time required for bead clearance of ciliated lung tissue when treated with a control composition, a CSA-131 composition without pluronic, and CSA-131 compositions with varying concentrations of pluronic from 1-5%.

TABLE 2

Number of explants (out of 12) clearing beads during the indicated amount of time after incubation with CSA-131 (100 μg/mL) for 1 h. The control was not treated with CSA-131. Indicated amounts of pluronic were used with ceragenin.
Time Required for Bead Clearance

| Pluronic | <10 min | <20 min | <30 min | No Clearance |
|---|---|---|---|---|
| Control | 10/12 | 2/12 | — | — |
| 0% | 3/12 | 2/12 | 1/12 | 6/12 |
| 1% | 4/12 | 2/12 | 1/12 | 5/12 |
| 2% | 7/12 | 3/12 | 2/12 | — |

TABLE 2-continued

Number of explants (out of 12) clearing beads during the indicated amount of time after incubation with CSA-131 (100 μg/mL) for 1 h. The control was not treated with CSA-131. Indicated amounts of pluronic were used with ceragenin.
Time Required for Bead Clearance

| Pluronic | <10 min | <20 min | <30 min | No Clearance |
|---|---|---|---|---|
| 3% | 7/12 | 4/12 | 1/12 | — |
| 4% | 8/12 | 4/12 | — | — |
| 5% | 10/12 | 2/12 | — | — |

Scanning Electron Microscopy of Cilia on Porcine Trachea

Explants (5 $mm^3$) were washed gently in Sorensen buffer (0.1 M, pH 7.2) to remove mucus and secretions. The fixative compounds were all diluted in the Sorensen buffer. The trachea pieces were incubated for 24 h with 2% of glutaraldehyde (Electron Microscopy Sciences, Hatfield, PA, USA) at 4° C. and then rinsed five times in Sorensen buffer. Additional post-fixation was performed using 1% of $OsO_4$ (Electron Microscopy Sciences, Hatfield, PA, USA) for 1.5 h under the hood at room temperature. After fixation, $OsO_4$ was removed by rinsing the explants at least seven times in Sorensen buffer and then explants were dehydrated in increasing concentrations of ethanol: 10, 30, and 50, each step for 15-20 min. The process was completed inside critical dryer baskets with 70% and 95% ethanol finishing twice in 100% for 15-20 min. Samples were then submerged in 100% ethanol in the critical point dryer at the critical point of carbon dioxide. Prepared samples were mounted on aluminum stands and then sputter coated with 5-10 nm of a gold-palladium alloy and observed with SEM (FEI Helios NanoLab 600 SEM/FIB, Hillsboro, OR, USA) at 5 kV.

To visualize the impacts of treatment of CSA-131, with and without pluronic, on cilia, scanning electron microscope (SEM) images were obtained of explants that had been treated with CSA-131 (100 μg/mL) alone and with pluronic (4%).

Figures 6A, 6B, 6C:
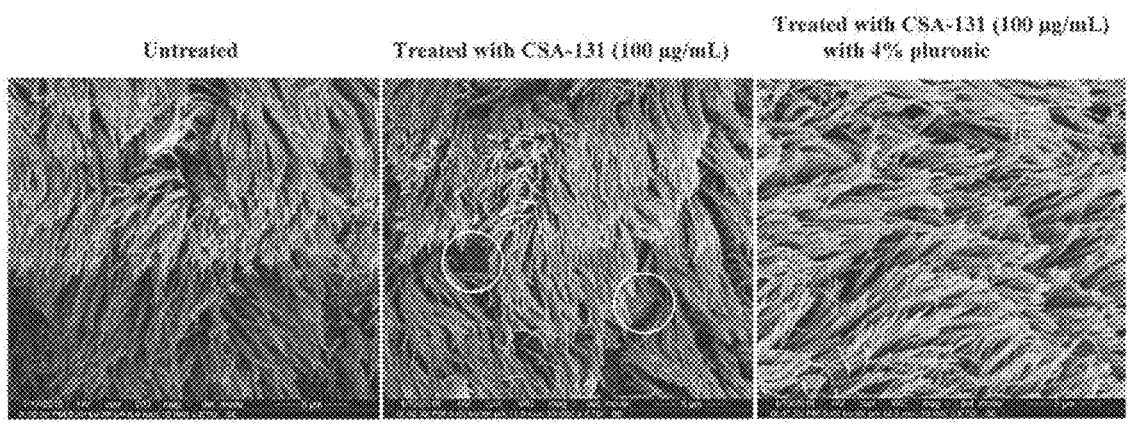
FIG. 6A is an SEM image of untreated and undamaged cilia on a porcine trachea explant.
FIG. 6B is an SEM image of cilia on a porcine trachea explant after being treated with a CSA composition of high concentration without micelles, with visible damage to the cilia.
FIG. 6C is an SEM image of cilia on a porcine trachea explant after being treated with a CSA composition of high concentration with micelles, with no visible damage to the cilia.

FIG. 6A is an SEM image of untreated and undamaged cilia on a porcine trachea explant. With the untreated explant, intact cilia were observed without exposure of the underlying goblet or epithelial cells.

FIG. 6B is an SEM image of cilia on a porcine trachea explant after being treated with a CSA composition of high concentration without micelles, with visible damage to the cilia. Exposed goblet cells are circled in the image of the sample treated with CSA-131 without pluronic. In the explant treated with CSA-131 alone, exposed goblet cells were observed, suggesting that some loss of cilia had occurred. This loss correlated with decreased cilia function in the bead clearance assay.

FIG. 6C is an SEM image of cilia on a porcine trachea explant after being treated with a CSA composition of high concentration with micelles, with no visible damage to the cilia. In contrast to FIG. 6B, with the explant treated with CSA-131 with pluronic (4%), a fully intact cilia bed was observed with no exposure of goblet or epithelial cells. This treatment did not influence bead clearance, and also it did not appear to influence the cilia bed.

Ex Vivo Efficacy Evaluation

Tests verified that CSA-131, formulated with pluronic, was able to eradicate microorganisms in tissue from the trachea and lung. For these studies, explants were infected with either C. albicans or C. auris then treated with CSA-131 alone or with pluronic (4% or 5%). Using 5 $mm^3$ explant cubes of porcine trachea and lung, ex vivo antifungal efficacy experiments were conducted. Cubes were dissected using a sterile razor blade form the ventral surface of the left caudal lobe of three sets of porcine lungs. After trimming excess tissues away from the explants to produce uniform of size (5 mm), explants were incubated at 37° C. in DMEM/RPMI inoculated with 106 CFU/explant of C. auris (CDC 0384) or C. albicans (ATCC 90028) in a 48-well plate. Explants were treated after 2 h of incubation with CSA-131 in the presence or absence of pluronic. Treated explants were incubated for 24 h at 37° C. After incubation, tissues were suspended in 250 μL of neutralizing broth and vortex on the highest setting for 4 min. Samples were then serially diluted in PBS, plated on 5% sheep blood TSA plates, and incubated at 37° C. for 48 h.

Figure 7A:
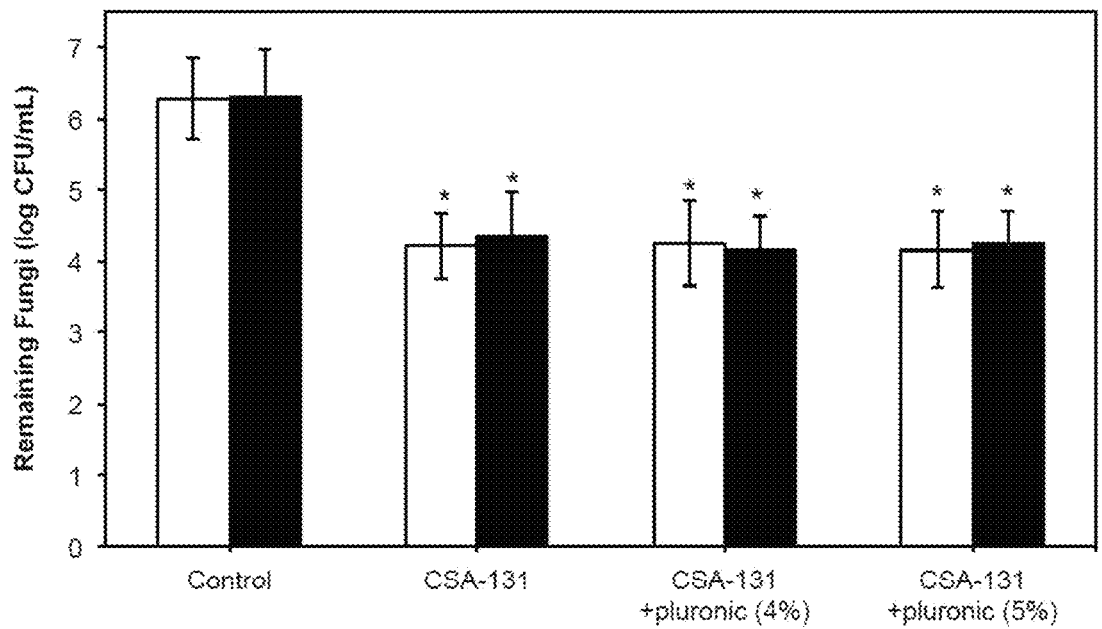
FIG. 7A is a bar graph showing a test on trachea explants comparing the antifungal activity of CSA compositions with and without micelles on fungi, and against a control without any CSA.
Figure 7B:
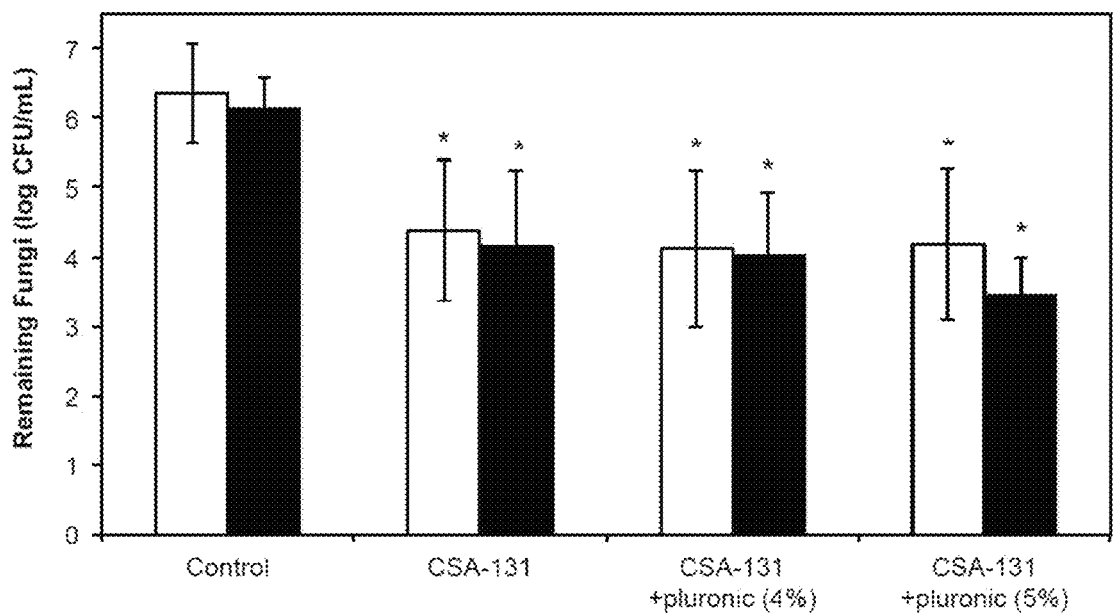
FIG. 7B is a bar graph showing a test on lung explants comparing the antifungal activity of CSA compositions with and without micelles on fungi, and against a control without any CSA.

FIGS. 7A and 7B are bar graphs comparing the antifungal activity of CSA compositions with and without micelles on fungi, and against a control without any CSA. White bars shown remaining C. albicans (ATCC 90028); black bars show remaining C. auris (CDC 384). FIG. 7A shows a test conducted using trachea explants; FIG. 7B shows a test conducted using lung explants. In control explants, fungal counts were over six logs in both tissue types. From treated explants, fungal counts were one and a half to two logs less (a decrease of up to 99%). Differences from controls were statistically significant (p<0.05), but small differences between results with CSA-131 alone and CSA-131 with pluronic (4% or 5%) were not significant. Interestingly, there was no significant difference of fungal growth in the tracheal and lung explants.

VII. Conclusion

Bacteria and fungi are both important pathogens in the trachea and lung, and infections are increasingly recognized as polymicrobial. Consequently, effective development of new therapies should target a broad spectrum of bacteria and fungi. In addition, persistent infections, including those associated with CF, involve biofilm components, which adds an antibiofilm component to therapy development. AMPs play important roles in controlling microbial growth in these tissues; however, it is evident that in some situations these innate immune defenses fail to fully protect the trachea and lung. Considerations of means of augmenting the activities of AMPs are complicated by the susceptibility of cilia to damage, and since they play vital roles in these tissues, potential treatments must take into account impacts on cilia. Ceragenins have been shown to have potent activity against pathogens associated with the trachea and lung, including the ability to eradicate established biofilms. Nevertheless, concentrations of ceragenin CSA-131 necessary to eliminate biofilms cause cilia damage. To mitigate these effects on cilia, we employed the poloxamer Pluronic® F-127. The association of CSA-131 with micelles formed by this surfactant does not alter antimicrobial activity against planktonic or biofilm forms of targeted microorganisms. However, with pluronic, the impact of CSA-131 on cilia is abolished. Ex vivo studies of CSA-131 with pluronic demonstrate the ability of this ceragenin to substantially reduce numbers of pathogenic strains of fungi in tissue. As a mimic of AMPs and with the protective effects of pluronic, ceragenin CSA-131 appears to be well suited for the treatment of polymicrobial and biofilmrelated infections.

The invention claimed is:

1. A method of therapeutically or prophylactically treating a microbial infection of ciliated tissue of a subject in need thereof, the method comprising:
providing a treatment composition including:
a cationic steroidal antimicrobial (CSA) compound comprising CSA molecules,
a poloxamer, and
a carrier,
wherein the poloxamer is included in an amount and combined with the CSA compound in a manner so that the CSA compound is encapsulated in and stabilized by micelles formed by the poloxamer so as to decrease cytotoxicity of the CSA compound to ciliated tissue,
wherein the poloxamer is included in the treatment composition in an amount, by weight, that is about 100 to 1000 times the amount of the CSA compound, by weight,
wherein at least 75% of the CSA molecules are individually sequestered CSA molecules or particles less than 1 μm in size; and
administering the treatment composition to the ciliated tissue of the subject in need thereof;
wherein the treatment composition therapeutically or prophylactically treats the microbial infection by killing or deactivating microbes associated with the ciliated tissue without disrupting ciliary function.

2. The method of claim 1, wherein the microbes associated with the ciliated tissue include biofilm.

3. The method of claim 1, wherein the microbes associated with the ciliated tissue include bacteria and/or fungi.

4. The method of claim 1, wherein the CSA compound is included in the treatment composition at a concentration of about 5 μg/ml to 200 μg/ml.

5. The method of claim 1, wherein the poloxamer is included in the treatment composition at a concentration of about 0.5% to about 20% by weight of the treatment composition.

6. The method of claim 1, wherein the poloxamer is included in the treatment composition in an amount, by weight, that is about 250 to 750 times the amount of the CSA compound, by weight.

7. The method of claim 1, wherein the poloxamer has a polyoxypropylene section with a molecular weight of about 2,500 to 5,500 g/mol, and the polyoxyethylene content ranges from about 50% to 90%.

8. The method of claim 1, wherein the poloxamer is poloxamer 407.

9. The method of claim 1, wherein less than 25% of the CSA molecules form agglomerates or particles 1 μm or larger in size.

10. The method of claim 1, wherein the ciliated tissue is tissue of the upper respiratory tract, sinuses, lungs, trachea, fallopian tubes, uterus, or ependyma.

11. The method of claim 1, wherein the treatment composition is administered via inhalation.

12. The method of claim 11, wherein the treatment composition is administered as an aerosol or a spray.

13. The method of claim 1, wherein the CSA compound is CSA-131.

14. The method of claim 1, wherein the treatment composition is coated onto a medical device that is contacted to the ciliated tissue.

15. A method of therapeutically or prophylactically treating a microbial infection of ciliated tissue of the upper respiratory tract, sinuses, lungs, or trachea of a subject in need thereof, comprising:
providing a treatment composition including:

a cationic steroidal antimicrobial (CSA) compound comprising CSA molecules, a poloxamer, and a carrier comprising a medical device on which the CSA compound and poloxamer are applied, wherein the poloxamer is included in an amount and combined with the CSA compound in a manner so that the CSA compound is encapsulated in and stabilized by micelles formed by the poloxamer so as to decrease cytotoxicity of the CSA compound to ciliated tissue, wherein the poloxamer is included in the treatment composition in an amount, by weight, that is about 100 to 1000 times the amount of the CSA compound, by weight, wherein at least 75% of the CSA molecules are individually sequestered CSA molecules or particles less than 1 μm in size; and administering the treatment composition to the ciliated tissue of the upper respiratory tract, sinuses, lungs, or trachea in the subject in need thereof by placing the medical device in the upper respiratory tract, sinuses, lungs, or trachea of the subject;

wherein the treatment composition therapeutically or prophylactically treats the microbial infection by killing or deactivating microbes associated with the ciliated tissue without disrupting ciliary function.

16. The method of claim 15, wherein the microbes associated with the ciliated tissue include biofilm.

17. The method of claim 16, wherein the microbes include bacteria and/or fungi.

18. A method of therapeutically or prophylactically treating a microbial infection of ciliated tissue of the lung(s) of a subject in need thereof, the method comprising:

providing a treatment composition including:

a cationic steroidal antimicrobial (CSA) compound comprising CSA molecules;

a poloxamer; and a carrier, wherein the poloxamer is included in an amount and combined with the CSA compound in a manner so that the CSA compound is encapsulated in and stabilized by micelles formed by the poloxamer so as to decrease cytotoxicity of the CSA compound to ciliated tissue, wherein the poloxamer is included in the treatment composition in an amount, by weight, that is about 100 to 1000 times the amount of the CSA compound, by weight, wherein at least 75% of the CSA molecules are individually sequestered CSA molecules or particles less than 1 μm in size; and administering the treatment composition to the ciliated tissue of the lung(s) in the subject in need thereof;

wherein the treatment composition therapeutically or prophylactically treats the microbial infection by killing or deactivating microbes associated with the ciliated tissue without disrupting ciliary function.

19. The method of claim 18, wherein the microbes associated with the ciliated tissue include at least one of biofilm, bacteria, or fungi.

20. The method of claim 18, wherein the CSA compound is CSA-131.

* * * * *